United States Patent [19]

Coffen et al.

[11] Patent Number: 4,789,750

[45] Date of Patent: Dec. 6, 1988

[54] 2-(TRIMETHYL-TRIDECENYL)-TETRAMETHYLCHROMAN INTERMEDIATES FOR VITAMIN E

[75] Inventors: David L. Coffen, Glen Ridge, N.J.; Rudolf Schmid, Munchenstein, Switzerland; Mark J. Sebastian, Plainfield, N.J.

[73] Assignee: Hoffman-La Roche Inc., Nutley, N.J.

[21] Appl. No.: 30,798

[22] Filed: Mar. 27, 1987

[51] Int. Cl.$^4$ .................................. C07D 311/72
[52] U.S. Cl. ........................... 549/407; 549/408; 549/274; 560/261
[58] Field of Search ........................................ 549/407

[56] References Cited

PUBLICATIONS

Ladner et al., J. Am. Chem. Soc. 106, 7250 (1984).
Crout et al., J. Chem. Soc., Chem. Commun, 1986 p. 808.
Whitesides, Angew, Chem. Int. Ed. 24, 1985, 617–638.
Findeis et al., Ann. Reports in Med. Chem., 19, 263 (1984).
Saucy, Organic Syntheses, 63, 1984, 198, 199.
Trost, Compreh. Organomet. Chem., 8, 1980, 800, 819–820.
Trost, J. Am. Chem. Soc., 103, 1864 (1981).
Trost, J. Org. Chem. 49, 468 (1984).
Trost, Tetrahedron, 33, 1977, 2615–2649.
Tsuji, Organic Synthesis with Palladium Compounds, Springer-Verlag, 1980, 37–51.

*Primary Examiner*—Nicky Chan
*Attorney, Agent, or Firm*—Jon S. Saxe; George M. Gould; William H. Epstein

[57] ABSTRACT

6-Etherified hydroxy -2-(4',8',12'-trimethyl-5'-tridecenyl)-2,5,7,8-tetramethylchromans with an oxo or hydroxy substituent at the 2' position which may be substituted with an arylsulfonyl or a carboxyalkyl at the 3' position and containing a single or double bond at the 11 position, said chromans being intermediates for producing natural vitamin E.

16 Claims, No Drawings

2-(TRIMETHYL-TRIDECENYL)-TETRAMETHYL-CHROMAN INTERMEDIATES FOR VITAMIN E

SUMMARY OF THE INVENTION

This invention provides a novel synthesis for vitamin E which has the structure

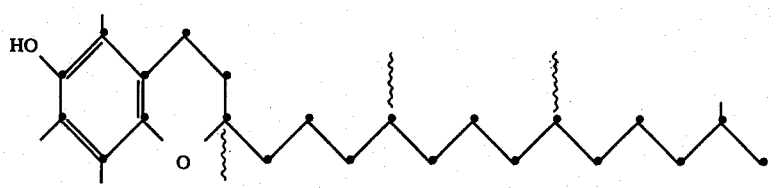

I through the reaction in the presence of a palladium containing catalyst, of a compound of the formula:

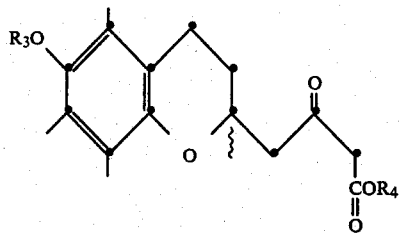

II wherein $R_4$ is lower alkyl; and $R_3$ taken together with its attached oxygen atom forms an ether hydroxy protection group with a compound of the formula:

III

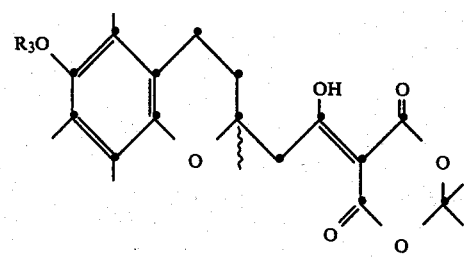

IV wherein the dotted bond represents an unsaturated bond or an unsaturated bond which is hydrogenated; and R taken together with its attached oxygen atom forms an hydrolyzable ester hydroxy protecting group or through the reaction of a compound of the formula wherein $R_3$ is as above with a compound of the formula

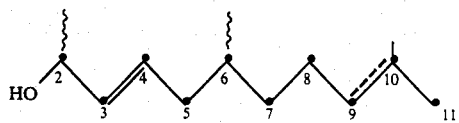

V wherein the dotted bond is as above; followed by treatment with a palladium containing catalyst or through the catalyzed reaction of a compound of the formula

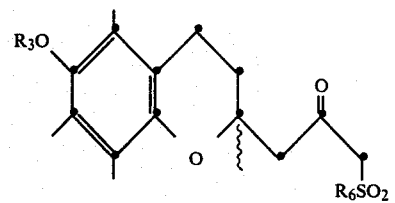

VI wherein $R_6$ is aryl or lower alkyl and $R_3$ is as above with a compound of the formula III.

The process of this invention can be utilized to produce the compound I in any of its stereo configurations including naturally occurring optically active vitamin E which has the formula

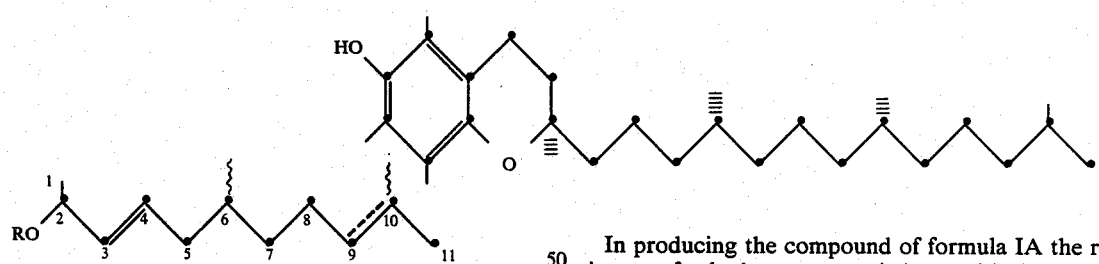

I-A

In producing the compound of formula IA the reactions set forth above are carried out with the optically active forms of the compound of formulas II, III, IV, V and VI, i.e.,

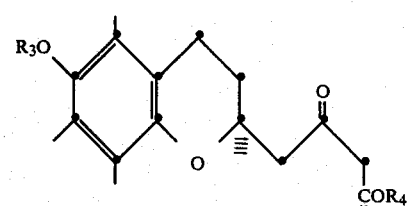

II-A

III-A

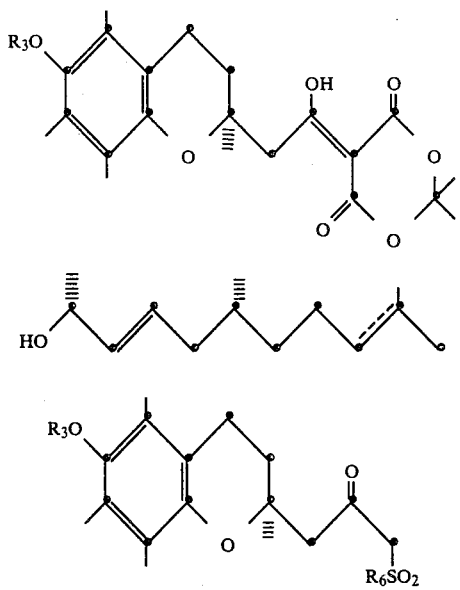

wherein the dotted bond, R, $R_3$, $R_4$ and $R_6$ are as above.

DETAILED DESCRIPTION

As used throughout this application, the term "lower alkyl" includes both straight chain and branched chain alkyl groups having from 1 to 7 carbon atoms such as methyl and ethyl. As used herein, the term "lower alkoxy" dneotes lower alkoxy groups containing 1 to 7 carbon atoms preferably 1 to 7 carbon atoms, such as methoxy, ethoxy, i-propoxy, t-butoxy, etc. As also used herein, the term "lower alkanoic acid" comprehends an alkanoic acid of from 1 to 7 carbon atoms such as formic acid and acetic acid. The term "lower alkanoyl" designates the monovalent radical formed from a lower alkanoic acid by removal of the OH group on the COOH moiety. Among the preferred lower alkanoyl groups are acetyl, pivaloyl, butyryl, propionyl with acetyl being especially preferred. As further used herein, the term "halogen" of "halo", unless otherwise stated, comprehends all halogens such as fluorine, chlorine, bromine and iodine. Alkali metal includes all alkali metals such as lithium, sodium and potassium.

In the pictorial representation of the compounds given throughout this application, a thickened taper line (Δ) indicates a substituent which is in the beta-orientation (above the plane of the molecule), a broken line (=) indicates a substituent which is in the alpha-orientation (below the plane of the molecule) and a wavy line ($\}$) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, which can be unsubstituted or substituted in one or more positions with a lower akylenedioxy, nitro, halo, a lower alkyl or a lower alkoxy substituent, and polynuclear aryl groups such as naphthyl, anthryl, phenanthryl, etc., which can be unsubstituted or substituted with one or more of the aforementioned groups. The preferred aryl groups are the substituted and unsubstituted mononuclear aryl groups, particularly phenyl.

The term "ether hydroxy protecting group" designates any ether group for protecting a hydroxy group which, upon acid catalyzed cleavage or hydrogenolysis yields the free hydroxy group. Suitable ether protecting groups are, for example, the tetrahydropyranyl, benzyl, t-butyl or 4-methoxy-tetrahydropyranyl ethers. Others are arylmethyl ethers such as benzhydryl, or trityl ethers or alpha-lower alkoxy lower alkyl ether, for example, methoxymethyl or tri(lower alkyl)silyl ethers such as trimethylsilyl ether diethyl-t-butylsilyl ether or dimethyl-tert-butylsilyl ether. Acid catalyzed cleavage is carried out by treatment with an organic or inorganic acid. Among the preferred inorganic acids are the mineral acids such as sulfuric acid, hydrohalic acid, etc. Among the preferred organic acids are lower alkanoic acids such as acetic acid, para-toluenesulfonic acid, etc. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out such cleavage, temperature and pressure are not critical and this reaction can be carried out at room temperature and atmospheric pressure.

The term "hydrolyzable ester hydroxy protecting group" denotes ester protecting groups where the hydroxy substituent is protected by esterification with an organic acid to form an ester which upon hydrolysis yields the free hydroxy substituent. Among the preferred hydrolyzable esters which can be utilized to protect the hydroxy group are those esters formed by reacting the hydroxy group with a lower alkanoic acid containing from 1 to 7 carbon atoms present acetic acid, propionic acid, butyric acid, as well as aroic acids such as benzoic acid and carbonic acids of the formula

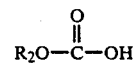

wherein $R_2$ is lower alkyl as well as lower alkoxy-lower alkanoic acids where the lower alkoxy is as above and the lower alkanoic acids contain from 2 to 7 carbon atoms.

The compound of formula V can be prepared from a compound of the formula:

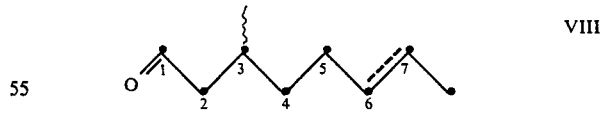

wherein the dotted bond is as above via the following intermediate

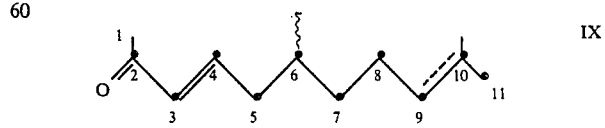

wherein the dotted bond is as above.

Compound of formula VIII is converted to the compound of formula IX by condensing the compound of formula VIII with acetone. Any of the conditions conventional in condensing aldehyde with acetone to produce an alpha, beta-unsaturated ketone can be utilized in carrying out this conversion. The compound of formula IX can be converted to the compound of formula V by treating the compound of formula IX with a reducing agent. Any conventional reducing agent, which will reduce a ketone to a hydroxy group can be utilized in carrying out this reaction. Among the conventional reducing agents are alkali metal aluminium hydrides, alkali metal borohydrides and aluminium isopropoxides. Any of the conditions conventionally utilized with respect to these reducing agents can be utilized in carrying out this reaction to produce the compound of formula V.

Where it's desirable to produce natural vitamin E, i.e. the compound of formula I-A, the compound of formula VIII is utilized where the methyl substituent at the 3-position has an R configuration. Condensation with acetone as described above, produces the compound of formula IX where the methyl substituent in the 6 position has the R configuration. The compound of formula V thus produced has the methyl substituent at the 6 position in the same configuration as in the compound of formula IX. In accordance with this invention, the compound of formula V can be converted by means of an enzymatic reaction into enantiomerically and diastereomerically pure compounds of formula III-A and V-A.

In converting the 2RS,6R compound of formula V to the 2R,6R compound of formula V-A, the compound of formula V is first esterified with a suitable hydrolyzable ester hydroxy protecting group such as those mentioned hereinbefore, to produce the compound of formula III where the methyl substituent at the 2-position is RS and the methyl substituent at the 6 position is 6R. In the compound of formula III, R is preferably a lower alkanoyl group most preferable butyryl. The esterification of the hydroxy group on the compound of formula V is carried out by conventional means, such as by reaction with a lower alkanolic acid, carbonic acid or reactive derivative thereof. The carbonate esters are formed in the usual manner by reacting the compound of formula V with a lower alkyl haloformate. The conditions conventional in preparing these lower alkanoyl ester and carbonate ester derivatives can be utilized in converting the compound of formula V into a suitable ester.

If it is desired to produce natural vitamin E, the 2RS,6R mixture of diastereomers of formula III can be converted into a mixture of the 2R,6R stereoisomer of formula V-A and the 2S,6R diastereomer of formula III-C by enzymatic hydrolysis. In accordance with this invention, it has been found that when the 2RS,6R compound of formula III is subjected to enzymatic hydrolysis utilizing an esterase enzyme, the compound of formula III in its 2RS form is specifically hydrolysed to produce the 2R,6R compound of formula V-A. This enzymatic reaction can be utilized to convert a 2RS compound of formula III to the 2S compound of formula III while keeping the same configuration of the methyl substituent at the 6-position. Therefore if a 2RS, 6RS compound of formula V is utilized, enzymatic hydrolysis provides the compound of formula III with a 2R,6RS configuration. On the other hand if a 2RS,6R compound of formula V is utilized, enzymatic hydrolysis produces the compound of formula III with a 2R,6R configuration.

This enzymatic hydrolysis produces the 2R compound of formula III above in admixture with the compound of formula

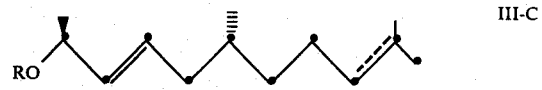

wherein the dotted bond and R are as above. The compounds of formula V-A and III-C can be easily separated.

In carrying out this enzymatic hydrolysis, the 2RS isomer of formula III dispersed in an aqueous medium is treated with an esterase enzyme. Any conventional esterase enzyme can be utilized to carry out this reaction. Among the esterase enzymes utilized in carrying out this reaction are lipases, particularly pancreatic lipases and lipases of bacterial and fungal origin. In carrying out this enzymatic hydrolysis, it is generally preferred to utilize the enzyme in a catalytically effective amount. As would be recognized, in order to achieve best results, the choice of a particular catalytically effective amount of enzyme will depend upon factors within the control of one skilled in the art. These factors include the amount of starting material, the enzyme source, the unit activity of the enzyme, the purity of the enzyme and the like. In carrying out this reaction, excesses of a catalytically effective amount of the esterase enzyme can be utilized. However, no additional beneficial results are to be achieved through the use of large excesses of enzyme.

In carrying out the enzymatic reaction, the compound of formula III is suspended in an aqueous medium. In suspending the compound of formula III in aqueous medium, emulsifying agents may be utilized to enhance the emulsification of the compound of formula III in the aqueous medium. Among the conventional emulsifying agents which can be utilized in accordance with this invention are included: sodium taurocholate, ammonium salts derived from fatty alcohols, and alkali metal salts of bile acids. If desired, the reaction medium can contain an inert organic solvent for the compound of formula III. Any conventional inert organic solvent which does not denature the enzyme can be utilized. Among the conventional solvents, are included acetonitrile, dimethylsulfoxide, etc. The enzymatic hydrolysis is carried out at a pH from 6 to 8, preferably at a pH of from 7.4 to 7.6. Any conventional method of maintaining the pH of the reaction mixture at the aforementioned pH can be utilized. Among the preferred methods is by means of buffers or automatic titration.

As stated above, the enzymatic hydrolysis of the compound of formula III produces the compound of formula V-A in admixture with the compound of formula III-C. These compounds can be easily separated once the enzymatic hydrolysis is stopped, by removing through filtration the enzyme from the reaction medium. Any conventional method of separation can be utilized to isolate the compound of formula V-A from the compound of formula III-C. Among the conventional means for separating these two compounds are included extraction and distillation.

The compound of formula III-A can be prepared by esterification as described hereinbefore from the compound of formula V-A produced through enzymatic hydrolysis. The compound of formula V-A can be converted to the compound of III-A by esterification such as described hereinbefore in connection with the conversion of the compound of formula V to the compound of formula III.

In the next step of the process of this invention, the compounds of formula II of formula II-A can be reacted with the compounds of formula III or III-A to produce an intermediate in the synthesis of vitamin E or its optically active isomers.

The compound of formula IV is formed from the compound of formula

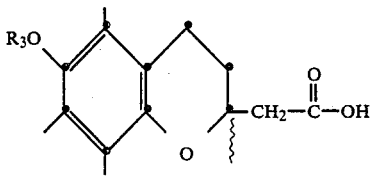

X wherein $R_3$ is as above via the following intermediate

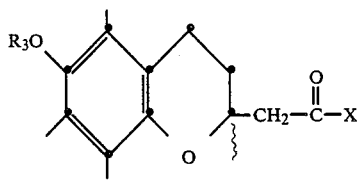

X-B wherein $R_3$ is as above and X is halogen. Where the compound of formula IV-A is desired, the compound of formula

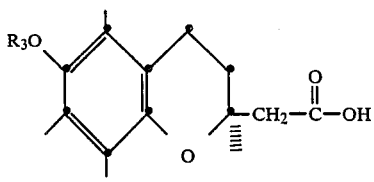

X-A is utilized as the starting material rather than the compound of formula X. The stereoconfiguration of the compound of formula X or X-A is carried through the entire process of this invention.

The compound of formula X or X-A is converted to the compound of formula X-B having the same stereoconfiguration as the compound of formula X or X-A by halogenation. Any conventional method of converting an organic acid to the corresponding acid halide can be utilized in this conversion. The compound of formula X-B is converted to the compound of formula IV by reacting the compound of formula X-B with Meldrum's acid according to conventional procedures such as disclosed by Oikawa, Sugano, et al., *J. Org. Chem.*, 1978, 43 2087; and Davidson, and Bernhardt, *J. Am. Chem. Soc.*, 1948, 70 3426. Through this reaction the compound of formula IV or the compound of formula IV-A is formed depending upon the stereo-configuration of the starting material, as illustrated by the compound of formula X or the compound of formula X-A.

The compound of formula IV or IV-A can be converted to the compound of formula II or II-A by refluxing the compound of formula IV or IV-A with a lower alkanol. The particular lower alkanol that is utilized becomes the substituent $R_4$ in the compound of formula II or II-A.

The compound of formula II or II-A is reacted with the compound of formula III or III-A to produce a compound of the formula

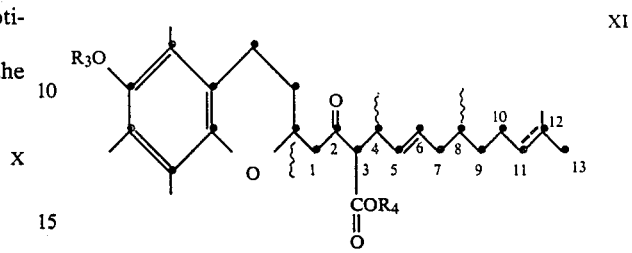

XI wherein $R_3$, $R_4$ and the dotted bond are as above. In the case where II-A is reacted with the compound of formula III-A, the methyl substituent at the 4 and 8 positions in the compound of formula XI have an R configuration. The place of joinder between the ring and the chain in this compound has an S configuration.

The above condensation to produce the compound of formula XI or any of the stereoisomers thereof is carried out in an organic solvent medium in the presence of a base and a catalyst which is an organic complex of zero valent palladium. Among the preferred catalysts are those complexes of palladium with tri(alkyl or aryl) phosphines. Among the particularly preferred catalysts for use in this reaction are palladium tetrakis(triarylphosphines).

In carrying out the above condensation reaction with a palladium complex as a catalyst, an organic solvent medium is utilized and the reaction proceeds at temperatures of from $-90°$ C. to $+25°$ C., with temperatures of from about $-78°$ to $-20°$ C. being preferred. Furthermore, the reaction is carried out in the presence of a strong base. Any strong base can be utilized, such as the alkali metal lower alkoxides, alkali metal hydrides or lower alkyl alkali metals. In carrying out this reaction, any conventional inert organic solvent can be utilized as the reaction medium. Among the preferred solvents are organic ethers and those organic solvents which are liquid at the reaction temperature utilized.

The compound of formula XI is converted to the compound of formula I or its various stereoisomers such as to compounds of formula I-A depending upon the stereoconfiguration of the methyl groups designated by the wavy line in the compound of formula XI Via the following intermediates.

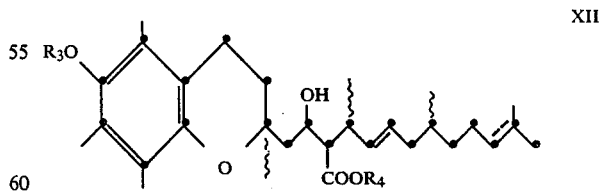

XII

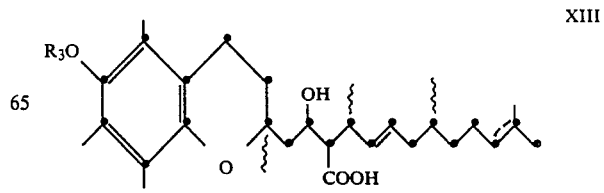

XIII

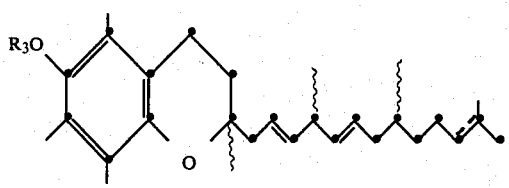

XIV wherein R₃, R₄ and the dotted line are as above.

In carrying out the conversion of the compound of formula XI to the compound of formula I or any of its desired stereoisomers such as the compounds of formula I-A, the configuration of the methyl substituents on the compound of formula XI is carried through to produce the compound of formula I having the desired stereo-configuration.

The compound of formula XI is converted to the compound of formula XII by treatment with a reducing agent. Any conventional reducing agent which reduces oxo groups to hydroxy groups can be utilized in carrying out this procedure. The preferred reducing agents are alkali metal borohydride with sodium borohydride being particularly preferred. Any of the conditions conventionally used with these reducing agents can be utilized to carrying out this conversion. The compound of formula XII is converted to the compound of XIII by ester hydrolysis. Any of the conditions conventional in ester hydrolysis can be utilized to carry out this conversion. The compound of formula XIII is converted to the compound of formula XIV by treating the compound of formula XIII with a diloweralkoxy acetal of a dilower alkyl formamide, in accordance with the standard reaction disclosed by Ruettimann, et al. in *Helv. Chim. Acta.*, 58, 1451 (1975). The compound of formula XIV is converted directly to the compound of formula I or its various stereoisomers, such as the compound of formula I-A by hydrogenation utilizing a conventional hydrogenation catalyst, such as platinum or palladium on carbon. Any of the conditions conventional for such hydrogenations can be utilized in this conversion.

On the other hand, the compound of formula IV or its various stereoisomers such as the compound of formula IV-A can be converted to the compound of formula I or its various steroisomers such as the compound of formula I-A by first condensing the compound of formula IV or its various stereoisomers such as the compound of formula IV-A with the compound of formula V or its various stereoisomers such as the compound of formula V-A to produce

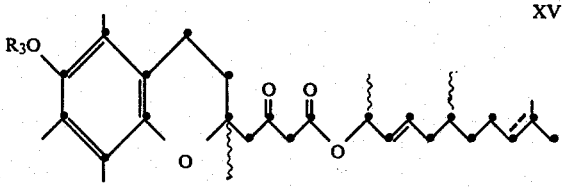

XV wherein R₃ and the dotted bond are as above and then converting the compound of formula XV to the compound of formula I or I-A via the following intermediates:

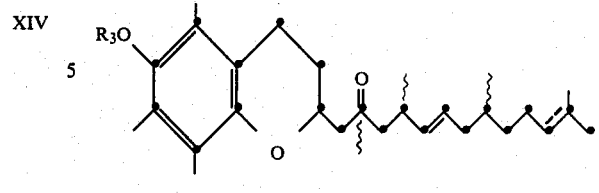

XVI

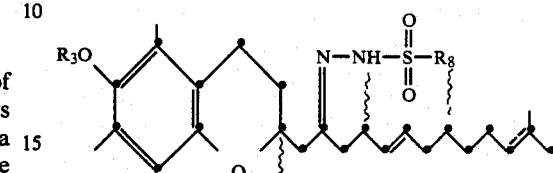

XVII

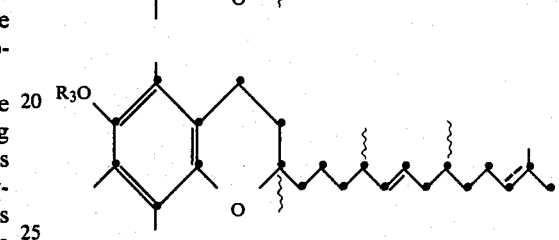

XIX wherein R₃ and the dotted bond is as above; and R₈ is aryl or lower alkyl.

The compound of formula IV or its various stereoisomers such as the compound of formula IV-A can be condensed with the compound of formula V or its various stereoisomers such as the compounds of formula V-A to produce the compound of formula XV. When the compound of formula IV-A is condensed with the compound of formula V-A, the compound of formula XV is produced carrying the methyl substituents represented by the wavy line are in the alpha orientation. This alpha orientation is continued throughout the compounds of formula XVI XVII and XIX to produce the compounds of formula I-A.

The condensation of the compound of formula IV with the compound of formula V is carried out by refluxing these two reactants in an inert organic solvent. In carrying out this reaction, any conventional inert organic solvent can be utilized. Preferably those inert organic solvents have a boiling point of 50° C. or greater. Among the preferred inert organic solvents are the high boiling hydrocarbon solvents such as toluene and xylene, etc.

The compound of formula XV is converted to the compound XVI by treating the compound of formula XV with a catalytically effective amount of a palladium containing catalyst such as those mentioned in connection with the condensation of the compound of formula II with the compound of formula III. Any conventional organic complex of zero valent palladium can be utilized in carrying out this reaction. Also in carrying out this reaction, any conventional inert organic solvent can be utilized. Among the preferred inert organic solvents are dimethylformamide and tetrahydrofuran or diethylether as well as hydrocarbon solvents such as toluene or xylene. This reaction can be carried out at any temperature from 20° C. to the reflux temperature of the reaction mixture. In carrying out this reaction with dimethylformamide or tetrahydrofuran or mixture thereof, temperatures of 20° C. is especially preferred. On the other hand, where hydrocarbon solvents such as toluene is utilized, temperatures of 50° C. are especially preferred. While, carrying out this reaction with greater than catalytic amount of the palladium catalyst can be utilized, such amounts do not generally provide any enhanced beneficial results. Therefore, in view of the added costs of such catalysts, higher amounts are seldom utilized.

The compound of formula XVII is converted to the compound of formula XVIII by reaction with a compound of the formula

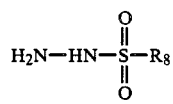
XX wherein $R_8$ is lower alkyl or aryl. The compound XVIII is then reacted with the alkali metal cyanoborohydride to produce the compound XIX. Both the reaction of the compound of formula XVII with the compound of formula XX to produce the compound of formula XVII and the conversion of the compound of formula XVII to produce the compound of formula XIX are carried out by conventional means in accordance with the Hutchins variation of the Wolff-Kishner reaction. See P. Hutchins., J. Am. Chem. Soc., 1973, 95, 3662. Hydrogenation is utilized in converting the compound of formula XIX to the compound of formula I or I-A. This hydrogenation can be carried out utilizing the same procedure described hereinbefore with respect to the conversion of a compound of formula XIV to the compound of formula I or I-A.

In accordance with another embodiment of this invention, the compound of formula I or its stereoisomers such as the compound of formula I-A is produced by reacting the compound of formula VI or any of its stereoisomers such as the compound of formula VI-A with the compound of formula III or any of its stereoisomers such as the compound of formula III to produce a compound of the formula

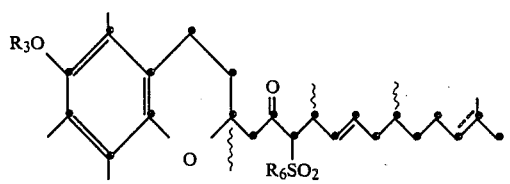
XXII wherein $R_3$, $R_6$ and the dotted bond are as above. This reaction is carried out in the same manner as described hereinbefore in connection with the condensation reaction of a compound of the formula II with a compound of the formula III to produce a compound of the formula XI.

The compound of formula XXII is converted to the compound of formula I through its conversion to a compound of formula XIV above. The conversion of the compound of formula XXII to the compound of formula XIV above proceeds via the following intermediates:

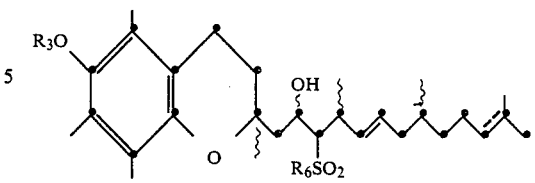
XXIII

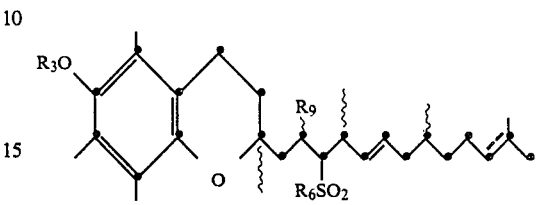
XXIV

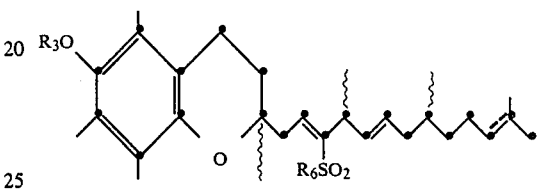
XXV wherein $R_3$, $R_6$ and the dotted line are as above and $R_9$ is a leaving group.

The compound of formula XXII is converted to the compound of formula XXIII by treatment with any reducing agent capable of converting an oxo group into a hydroxy group. Any conventional reducing agent capable of converting a ketone to a hydroxy group can be utilized in carrying out this reaction. Among the preferred reducing agents are the aluminium hydride reducing agents, such as diisobutylaluminium hydride reducing agents. Any of the conditions conventionally utilized with these reducing agents can be utilized to carry out this conversion.

The compound of formula XXII is converted to the compound of formula XXIV by converting the hydroxy group into a leaving group. Among the preferred leaving groups are halides, tosyloxy or mesyloxy. Any of the conditions conventional in converting a hydroxy group to a leaving group can be utilized in accordance with this procedure. The compound of formula XXIV is converted to the compound of formula XXV by elimination of the leaving group using conventional methods. The compound of formula XXI is converted to the compound of formula XIV by reductive cleavage in accordance with the Julia procedure described by J. Bremner, M. Julia, et al.; Tetrahedron Letters, 23, pg. 3265 (1982).

In preparing the compound of formula VI above, one starts from a compound of the formula

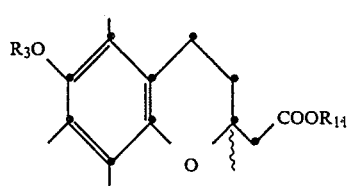
XXVI wherein $R_3$ is as above and $R_{11}$ is lower alkyl. If the compound of formula VI-A is desired, the methyl substituent represented by the wavy line is in the alpha-orientation. In fact any orientation of this methyl group may be used depending upon the desired stereo configuration of the compound of formula I.

In preparing the compound of formula VI, the compound of formula XXVI is condensed with a compound

wherein $R_6$ is as above.

This condensation is carried out in an inert organic solvent utilizing a strong base. Any of the bases mentioned hereinbefore can be utilized in carrying out this condensation. Furthermore, in carrying out this reaction, any inert organic solvent can be utilized. Among the preferred inert organic solvents are the ether solvents such as tetrahydrofuran. In carrying out this reaction, temperature and pressure are not critical and this reaction can be carried out at room temperature and atmospheric pressure. If desired, higher or lower temperatures can be utilized.

The invention is further illustrated by the following examples.

EXAMPLE 1

Preparation of (2Rs,3E,6R)-6,10-Dimethyl-3,9-undecadien-2-ol

A flame-dried 1 L 3-necked flask, fitted with a 30 cm Vigreux column topped with a distillation head, an argon inlet tube and a magnetic stirring bar, was charged with 36.8 g (0.189 mol) of (3E,6R)-6,10-dimethyl-3,9-undecadien-2-one (GC purity 93.6%), 500 mL of iospropanol and 40.0 g (0.196 mol) of aluminum isopropoxide. The reaction mixture was stirred and heated to gentle reflux under argon. Acetone was allowed to distill off at a rate of about 30 drops/min. While maintaining a head temperature of ca. 80° C. After 3.5 hours the reaction was shown by GC to be almost complete with 5% of starting material remaining. The reaction was cooled in an ice bath and the pressure was reduced to ca. 54 mmHg. Isopropanol was distilled off at a head temperature of 30° C.–31° C. until the reaction mixture was concentrated to a volume of about 200 mL. The residual oil was cooled in an ice bath, 200 mL of 2N HCl were carefully added with stirring and the mixture was poured into a separatory funnel containing 200 mL of ether. An additional 200 mL of 2N HCl were added to dissolve some remaining white solid material. The layers were separated and the aqueous phase was extracted with 2×200 mL of ether. The combined organic layers were washed successively with 200 mL of sat. NaHCO$_3$-solution and 200 mL of brine, dried over MgSO$_4$, filtered and concentrated on the rotovapor. The residue was dried at 0.1 mm for 30 minutes to afford 38.1 g (102.6%) of (2RS,3E,6R)-6,10-dimethyl-3,9-undecadien-2-ol as a light yellow liquid. GC analysis indicated a purity of 94.6%. This material was used as is in Example 2.

EXAMPLE 2

Preparation of (2RS,3E,6R)-6,10-Dimethyl-3,9-undecadien-2-yl butyrate

A flame-dried 0.5 L 3-necked round bottom flask equipped with a dropping funnel, a thermometer, a magnetic stirring bar and an argon inlet tube was charged with 36.5 g of (2RS,3E,6R)-6,10-dimethyl-3,9-undecadien-2-ol from Example 1 (GC purity 94.6%). After cooling in an ice bath, 29.3 g (0.371 mol) of pyridine (stored over KOH pellets), 33.8 g (0.214 mol) of butyric anhydride and 431 mg (3.5 mmol) of 4-N,N-dimethylaminopyridine were added while always keeping the internal temperature below 10° C. The cooling bath was removed and the mixture was stirred at ambient temperature for 1.5 hours. A GC analysis indicated no starting material remained. To the reaction mixture was then added carefully, in portions while stirring, 200 mL of sat, aqueous NaHCO$_3$ solution. After stirring for 30 minutes a total of 24 g of solid NaHCO$_3$ was added in portions at such a rate as to control the foaming, and the mixture was stirred for an additional period of 30 minutes. Subsequently, the reaction contents were poured onto 300 ML of deionized water and extracted with 3×300 mL of ether. The combined organic extracts were washed successively with 200 mL of deionized water, 2×200 mL of 2N HCl and 200 mL of brine, dried over MgSO$_4$, filtered and evaporated to afford 49.7 g of a light yellow liquid. Vacuum distillation through a 30 cm Vigreux column furnished (2RS,3E,6R)-6,10-dimethyl-3,9-undecadien-2-yl butyrate in the following fractions:

| Frac. | T(°C.) | mmHg | g | GC purity % | g. pure |
|---|---|---|---|---|---|
| 1 | 72–88 | 0.15–0.2 | 4.5 | 63 | 2.8 |
| 2 | 88–101 | 0.2–0.23 | 7.1 | 89.3 | 6.3 |
| 3 | 101–105 | 0.23–0.18 | 15.3 | 90.9 | 13.9 |
| 4 | 105–95 | 0.18–0.25 | 17.8 | 90.5 | 16.1 |
| residue | | | 3.3 | 43.7 | 1.1 |

This amounts to a weight yield of 44.7 (89.7%) of (2RS,3E,6R)-6,10-dimethyl-3,9-undecadien-2-yl buty-ate for fractions 1–4 or a chemical yield of 40.5 g (85.9%) based on GC purities of substrate and product.

EXAMPLE 3

Preparation of (R)-3,7-Dimethyloctanal

A 3 L indented flask equipped with a mechanical stirrer and a H$_2$ inlet was charged with 205.7 g (1.333 mol) of (R)-citronellal in 7.4 L of ethyl acetate. The flask was flushed with 0.1 cu. ft. of H$_2$ and 0.50 g (2.0 mmol) of platinum oxide were added. The reaction was stirred under a slight over-pressure of H$_2$ at ambient temperature for 124 hours. During this time, due to relatively rapid deactivation of the catalyst, an additional 3.50 g (143. mmol) of platinum oxide had to be added in 5 portions (0.5 g at 3.5 hours., 0.5 g at 22.5 hours., 1.0 g at 96.5 hours and 0.5 g at 121 hours). The course of the hydrogenation was monitored by GC analysis. After 124 hours, GC indicated the hydrogenation to be almost complete with 1.4% of starting material remaining. A total of 1.133 cu. ft. of hydrogen (theoretically 1.166 cu. ft.) had been consumed. The catalyst was removed by filtration through a pad od Celite (diatomeaceous earth). The clear filtrate was combined with the filtrate from a previously run, analogous reduction of 10.0 g (64.8 mmol) of (R)-citronellal and concentrated on the rotovapor. Vacuum distillation of the obtained pale yellow liquid through a 30 cm Goodloe column afforded the (R)-3,7-dimethyloctanal in following fractions:

| Frac. | T(°C.) | mmHg | g | GC purity % | g. pure |
|---|---|---|---|---|---|
| 1 | 38 | 0.3–0.18 | 23.15 | 89.1 | 20.9 |
| 2 | 38–36 | 0.18 | 9.7 | 90.9 | 8.8 |
| 3 | 36 | 0.18 | 34.7 | 94.7 | 32.9 |

-continued

| Frac. | T(°C.) | mmHg | g | GC purity % | g. pure |
|---|---|---|---|---|---|
| 4 | 36–31 | 0.15 | 29.0 | 96.7 | 28.0 |
| 5 | 31–33 | 0.15 | 67.6 | 98.3 | 66.5 |
| 6 | 47–90 | 0.25–0.13 | 21.0 | 13.4 | 2.8 |

This corresponds to a weight yield of 164.5 g (77%) of (R)-3,7-dimethyloctanal from fractions 1–5 or a chemical yield of 159.9 g (77.8%) of this compound based on GC purities of substrate and products.

EXAMPLE 4

Preparation of (3E,6R)-6,10-Dimethyl-3-undecen-2-one

A 3L 3-necked flask fitted with a reflux condenser, a mechanical stirrer and an argon inlet tube was charged with 161.5 g (1.033 mol) of (R)-3,7-dimethyloctanal (fractions 1–5 from Example 3, GC purity 97.3%), 413 mL of acetone and 1.24 L of 1% aq. KOH. The reaction mixture was stirred vigorously and refluxed for 48 hours. The course of the reaction was monitored by GC. The amount of starting material present was 5% after 25 hours and 3.6% after 48 hours. After cooling in an ice bath, the reaction mixture was poured into a separatory funnel containing 200 mL of brine and extracted with 3×800 mL of hexane/ether 1:1 (parts by volume). The combined organic fractions were washed with 300 mL of brine, dried over MgSO₄, filtered and evaporated. Vacuum distillation of the residue through a 30 cm Vigreus column afforded (3E,6R)-6,10-dimethyl-3-undecen-2-one in the following fractions:

| Frac. | T(°C.) | mmHg | g | GC purity % | g. pure |
|---|---|---|---|---|---|
| 1 | 30–85 | 0.1–0.08 | 22.1 | 65.5 | 14.5 |
| 2 | 85–87 | 0.08 | 47.0 | 86.2 | 40.5 |
| 3 | 87–89 | 0.08–0.15 | 105.5 | 91.3 | 96.3 |
| 4 | 90–100 | 0.13 | 14.8 | 52.4 | 7.8 |

The weight yield of (eE,6R)-6,10-dimethyl-3-undecen-2-one is therefore 189.4 g (93.4%) and the chemical yield based on GC purities of substrate and products is calculated to be 159.1 g (81.0%).

EXAMPLE 5

Preparation of (2RS,3E,6R)-6,10-Dimethyl-3-undecen-2-ol

A flame-dried 3L 3-necked flask fitted with a 30 cm Vigreux column topped with a distillation head, an argon inlet tube and a magnetic stirring bar was charged with 131.5 g (0.670 mol) of (3E,6R)-6,10-dimethyl-3-undecen-2-ol ml (from Example 4, fractions 2 and 3, GC purity 90%), 1.60 L of isopropanol and 137.9 g (0.70 mol) of aluminum isopropoxide. The reaction mixture was stirred and heated to gentle reflux. Acetone was allowed to distill off at a rate of about 30 drops/minute while maintaining a head temperature of 60°–80° C. After 2.5 hours the reaction tended to become sluggish with ca. 5% of starting ketone remaining by GC analysis. Therefore, an additional 300 mL of isopropanol and 13.9 g (0.07 mol) of aluminum isopropoxide were added and the reaction was refluxed for a further 1 hour, after which the amount of starting ketone had decreased to 3.0%. The reaction was cooled and the pressure was reduced to about 65 mmHg. Isopropanol was distilled off at a head temperature of 35° C. until the volume of the reaction mixture was reduced to ca. 300 mL To the cooled mixture were added carefully with stirring 500 mL of 2N HCl. After most of the initially precipitated white solid had dissolved, the mixture was poured onto 300 mL of 2N HCl and 300 mL of ether. The layers were separated and the aqueous phase was extracted with 2×600 mL of ether. The combined organic fractions were washed successively with 300 mL of deionized water, 300 mL of sat. aqueous NaHCO₃ solution and 300 mL of brine, dried over MgSO₄, filtered and evaporated to afford crude (2RS,3E,6R)-6,10-dimethyl-3-undecen-2-ol, GC purity 85%. Vacuum distillation through a 30 cm Goodloe column afforded (2RS,3E,6R)-6,10-dimethyl-3-undecen-2-ol in the following fractions:

| Frac. | T(°C.) | mmHg | g | GC purity % | g. pure |
|---|---|---|---|---|---|
| 1 | 62–72 | 0.15–0.2 | 8.9 | 43.1 | 3.8 |
| 2 | 72 | 0.3 | 20.6 | 75.1 | 15.5 |
| 3 | 73–75 | 0.32–0.28 | 12.2 | 83.2 | 10.2 |
| 4 | 73 | 0.33 | 14.2 | 86.2 | 12.2 |
| 5 | 74.5 | 0.3–0.28 | 7.3 | 89.2 | 6.5 |
| 6 | 74–73 | 0.2 | 59.2 | 95.2 | 56.4 |

This corresponds to a weight yield (2RS,3E,6R)-6,10-dimethyl-3-undecen-2-ol of 128.3 g (87.6%) for fractions 1–7 and the chemical yield, based on GC purities of substrate and product, calculates for 110.0 g (85%).

EXAMPLE 6

Preparation of (2RS,3E,6R)-6,10-Dimethyl-3-undecen-2-yl butyrate

A flame-dried 1 L 3-necked flask equipped with a dropping funnel, a thermometer, an argon inlet tube and a magnetic stirring bar was immersed in an ice bath and charged with 97.8 g (0.493 mol) of (2RS,3E,6R)-6,10-dimethyl-3-undecen-2-ol (fractions 3–6 from Example 5, GC purity 91.8%), 74.3 g (0.94 mol) of pyridine (stored over KOH pellets), 86.1 g (0.54 mol) of butyric anhydride and 1.10 g (9 mmol) of 4-N,N-dimethylaminopyridine. The additions of the reagents were carried out at such a rate as to maintain the internal temperature at below 10° C. The cooling bath was removed and the solution was stirred at ambient temperature.

After 75 minutes of stirring, a GC analysis showed no more starting alcohol remaining. The reaction was then quenched carefully with 200 mL of sat. aqueous NaHCO₃ solution and ca. 60 g of solid NaHCO₃ in small portions at such a rate as to control the foaming. After stirring for 1 hour, the mixture was poured into 400 mL of deionized water and 600 mL of hexanes. The layers were separated and the aqueous phase was extracted with 2×400 mL of hexanes. The combined organic fractions were washed successively with 2×200 mL of deionized water, 2×200 mL of 2N HCl and 300 mL of brine, dried over MgSO₄, filtered and evaporated to yield 129.8 g of (2RS,3E,6R)-6,10-dimethyl-2-yl butyrate as a clear colorless oil. Vacuum distillation through a 30 cm Goodloe column afforded (2RS,3E,6R)-6,10-dimethyl-3-undecen-2-yl butyrate in the following fractions:

| Frac. | T(°C.) | mmHg | g | GC purity % | g. pure |
|---|---|---|---|---|---|
| 1 | 81–84 | 0.33–0.35 | 1.9 | 18.3 | 0.35 |
| 2 | 86–95 | 0.35 | 4.4 | 60.0 | 2.64 |
| 3 | 96 | 0.35 | 3.8 | 71.4 | 2.7 |
| 4 | 96–97.5 | 0.43–0.45 | 3.5 | 75.2 | 2.6 |
| 5 | 97.5 | 0.45 | 4.3 | 80.4 | 3.5 |
| 6 | 97.5 | 0.45 | 3.0 | 80.6 | 2.4 |

| Frac. | T(°C.) | mmHg | g | GC purity % | g. pure |
| --- | --- | --- | --- | --- | --- |
| 7 | 98 | 0.40–0.45 | 4.9 | 79.6 | 3.9 |
| 8 | 98–99.5 | 0.5–0.4 | 17.6 | 83.7 | 14.7 |
| 9 | 97.5–100 | 0.38–0.33 | 31.1 | 90.0 | 28.0 |
| 10 | 97–95 | 0.33 | 35.6 | 91.4 | 32.5 |
| | | | | | 107.2 |

Fractions 2–10 (108.2 g) contained (2RS,3E,6R)-6,10-dimethyl-3-undecen-2-yl butyrate corresponding to a weight yield of 81.8%. The chemical yield based on GC purities of substrate and products calculates for 107.2 g (88.2%).

EXAMPLE 7

Enzymatic hydrolysis of (2RS,3E,6R)-6,10-Dimethyl-3,9-undecadien-2-yl butyrate to yield [2R,3E,6R]-6,10-dimethyl-3,9-undecadien-2-ol A. With Pancreatin from Porcine Pancreas To a 2 L, three necked indented flask equipped with a mechanical stirrer, pH electrode and pH controller and a solenoid operated addition burette filled with 4N NaOH was added 355 mL of pH 8.0, 0.05M phosphate buffer, 354 mL of tap water, 11.42 g (0.0212 mol) of sodium taurocholate (from ox bile, crude), and 200 g of (2Rs,3E,6R)-6,10-dimethyl-3,9-undecadien-2-yl butyrate (0.750 mol resp. 0.656 mol based on a GC purity of 87.5%). The mixture was stirred vigorously and 14.1 g of pancreatin (grade II, from Porcine Pancreas) was added. The pH was adjusted to 7.5 by addition 13 mL pf 4N NaOH. The reaction was then run at ambient temperature within a pH range of 7.4–7.6 maintained by automatic addition of 4N NaOH. The reaction progress was monitored by GC analysis and NaOH consumption. A specific activity of 34.5 units/g pancreatin was calculated from the consumption of 1.95 mL of 4N NaOH within the first 16 minutes of the reaction. After 23.5 hours, at a consumption of 36.35 mL of 4N NaOH (22% conversion), an additional 14.1 g of pancreatin was added and the reaction was continued for another 12 hours. The hydrolysis was stopped at a consumption of a total of 60.75 mL of 4N NaOH (37% conversion) by addition of 1.0 L of ethanol. The mixture was stirred overnight, filtered through a pad of Celite to remove crystallized phosphate salts, and the pad was washed with 2×400 mL of ethanol/water, 1:1 parts by volume. To the filtrate was added 500 mL of brine and 900 mL of hexanes/ether 1:1. The organic layer was separated and the aqueous layer was extracted with 3×900 mL of hexane/ether (1:1 parts by volume). The combined organic extracts were washed with 700 mL of brine, dried over $Na_2SO_4$, filtered and evaporated. The residue was distilled through a 50 cm Goodloe column to afford 30.3 g of the alcohol i.e. (2R,3E,6R)-6,10-dimethyl-3,9-undecadien-2-ol, b.p. 82°–84° C./0.5 mmHg, 17.1 g of mixed fractions of alcohol and butyrate and a pot residue containing only butyrate. The mixed fractions together with 3.0 g of material which had been retained in the column and which had been washed out with hexanes, were separated by chromatography on 240 g of silica gel. After elution of 3.2 g of butyrate with hexane/2% ethyl acetate, 19.8 g of alcohol i.e. (2R,3E,6R)-6,10-dimethyl-3,9-undecadien-2-ol was eluted with hexanes/24% ethyl acetate. Kugelrohr distillation of the alcohol at ca. 120° C./0.5 mm afforded 18.3 g of (2R,3E,6R)-6,10-dimethyl-3,9-undecadien-2-ol as a colorless liquid which was combined with the alcohol fraction from the distillation to give 48.6 g of (2R,3E,6R)-6,10-dimethyl-3,9-undecadien-2-ol, GC purity 94.9% (33% yield based on mass, 35.8% chemical yield based on GC purities).

B. Hydrolysis with Pancreatin from Porcine Pancreas

To a 1 L, three-necked indented flask equipped with a mechanical stirrer, a pH electrode and an addition burette filled with 2N NaOH, which was operated by a pH controller and a lab pump, was added 113 mL of tap water, 113 mL of pH 8.0, 0.05M phosphate buffer and 3.62 g (6.73 mmol) of sodium taurocholate (from ox bile, crude). The pH was adjusted to 7.5 with 85% $H_3PO_4$ and 69.8 g of (2RS,3E,6R)-6,10-dimethyl-3,9-undecadien-2-yl butyrate (0.262 mol. resp. 0.232 mol based on a GC purity of 88.5%) was added. Then, with stirring, 5.0 g of pancreatin was added and the pH was adjusted again to 7.5 by addition of 1.0 mL of 2N NaOH. The hydrolysis was carried out at ambient temperature within a pH range of 7.4–7.6 maintained by automatic addition of 2N NaOH. After 23 hours, at a consumption of 25.75 mL of 2N NaOH (22% conversion), an additional 5.0 g of pancreatin was added and the hydrolysis was continued for another 14 hours to a total consumption of 43.85 mL 2N NaOH (38% conversion). Samples of ca. 0.5 mL were periodically removed from the reaction mixture for d.e. determinations. Each sample was diluted in a test tube with ether and brine, and the organic layer was separated, dried over $Na_2SO_4$, decanted and evaporated. The residual alcohol/butyrate mixture was treated with BSTFA and subjected to GC analysis. At the indicated conversions the following (2R,6R)/(2S,6R) diastereomer ratios for the silylated alcohol and the butyrate were observed: a) 6:4% conv.: 86:14 and 47:53; b) 10.2% conv.: 90:10 and 45.5:54.5; c) 18.8% conv.: 91.8:8.2 and 40.5:59.5; d) 22.2% conv.: 92.8:7.2 and 39:61; e) 29.8% conv.: 91.6:8.4 and 33.67; f) 37.8% conv.: 89.6:10.4 and 26:74.

Work-up and isolation of the alcohol and the butyrate were carried out in the same way as described in part A of this Example to afford 18.5 g of alcohol (2R,3E,6R)-6,10-dimethyl-3,9-undecadien-2-ol, GC purity 96% (36% yield based on mass, 39% chemical yield based on GC purities).

C. Hydrolysis with Lipoprotein Lipase

A 100 mL, three-necked round-bottom flask equipped with a magnetic stirring bar, pH electrode and an addition burette filled with 2N NaOH, which was operated by a pH controller and a lab pump, was charged with 10.0 g of (2RS,3E,6R)-6,10-dimethyl-3,9-undecadien-2-yl butyrate (37.5 mmol resp. 32.8 mmol based on a GC purity of 87.4%), 50 mL of pH 7.0, 0.05M phosphate buffer, 50.3 mg of microbial lipoprotein lipase 1715 units/mg) and 160 mg of Triton X-100. The hydrolysis was carried out at ambient temperature within a pH range of 6.8–7.2 maintained by automatic addition of 2N NaOH. From the consumption of 0.35 mL of 2N NaOH within the first 18 minutes, the specific activity was calculated to be 0.77 units/mg lipoprotein lipase.

Samples of 2 drops were periodically removed from the reaction mixture for d.e. determinations as described in part B of this Example. At the indicated conversions the following (2R,6R)/(2S,6R) diastereomer ratios for the silylated alcohol and the butyrate were observed: (a)

10.5% conv.: 95.4:4.6 and 45.7:54.3; (b) 24% conv.: 95.9:4.1 and 36.6:63.4; (c) 46% conv.: 95.0:5.0 and 19.7:80.3. After 14.5 hours, at a total consumption of 7.6 mL (15.2 mmol) 2N NaOH (corresponding to 46.3% conversion), the reaction was quenched with 200 mL of ethanol. The mixture was stirred for several hours, then filtered through a pad of Celite and the pad was washed with 2×300 mL of ethanol/water, 1:1. The filtrate was poured into a separatory funnel containing 300 mL of brine and extracted with 3×500 mL of hexane/ether, 1:1 parts by volume. The combined extracts were washed with 300 mL of brine, dried over $Na_2SO_4$, filtered and evaporated to leave 9.2 g of a cloudy oil, which was chromatographed on 200 g of silica gel. Elution with hexane/2% ethyl acetate afforded, after Kugelrohr distillation, 5.6 g of (2S,3E,6R)-6,10-dimethyl-3,9-undecadien-2-yl butyrate, GC purity 85.5% (56% recovery based on mass, 55% chemical yield). Elution with hexanes/25% ethyl acetate then afforded 3.0 g of (2RS,3E,6R)-6,10-dimethyl-3,9-undecadien-2-ol, b.p. ca. 120°–140° C./0.4 mm, GC purity 94% (41% yield, 43.8% chemical yield) as a colorless liquid: $[\alpha]_D^{25} = +5.98°$ (2.04% in $CHCl_3$).

D. With Lipase from Pseudomonas

A 1L, three-necked indented flask equipped with a mechanical stirrer, a pH electrode and an addition burette filled with 2N NaOH, which was operated by a pH controller and a lab pump, was charged with 200 mL of pH 8.0, 0.05M phosphate buffer and 50 g of (2RS,3E,6R)-6,10-dimethyl-3,9-undecadien-2-yl butyrate (0.187 mol. resp. 0.164 mol based on a GC purity of 87.4%). The pH was adjusted to 7.5 by addition of a few drops of 85% $H_3PO_4$. Then 1.30 g of Triton X-100 and 2.08 g of lipoprotein lipase P "Amano" (from Pseudomonas sp., 30,000 u/g were added while stirring vigorously. The hydrolysis was carried out at ambient temperature within a pH range of 7.4–7.6 maintained by automatic addition of 2N NaOH. From the consumption of 0.95 mL of 2N NaOH within the first 16 minutes the specific activity was calculated to be 57 units/g lipase. Samples were periodically removed from the reaction mixture for d.e. determinations as described in part B of this Example. At the indicated conversions, the following (2R,6R)/(2S,6R) diastereomer ratios for the silylated alcohol and the butyrate were observedd: (a) 14.5% conv.: 97.5:2.5 and 36.64; (b) 30% conv.: 97.5:2.5 and 17:83; (c) 40% conv. 97.5:2.5 and 13:87. After 21.5 hours, at a consumption of 33.3 mL (66.6 mmol) 2N NaOH (corresponding to 40.6% conversion), the reaction was quenched with 250 mL of ethanol. The mixture was stirred for 4 hours, then filtered through a Celite pad and the pad was washed with 2×100 mL of ethanol/water, 1:1 parts by volume. The filtrate was poured onto 200 mL of brine, and extracted with 3×500 ml of hexane/ether, 1:1 parts by volume. The combined extracts were washed with brine, dried over $Na_2SO_4$, filtered and evaporated to leave 59.9 g of colorless liquid, which was chromatographed on 680 g silica gel. Elution with hexane/2% ethyl acetate afforded, after distillation 29.8 g of (2S,3E,6R)-6,10-dimethyl-3,9-undecadien -2-yl butyrate as a light yellow liquid, GC purity 85.6% (59.6% recovery, 58% chemical yield). Elution with hexane/25% ethyl acetate afforded, after Kugelrohr distillation at ca. 120°–150° C./0.6 mmHg, 12.6 g of (2R,3E,6R)-6,10-dimethyl-3,9-undecadien-2-ol as colorless liquid, GC purity 96.2% (34% yield; 37.6% chemical yield based on GC purities).

EXAMPLE 8

Enzymatic hydrolysis of (2RS,3E,6R)-6,10-Dimethyl-3-undecen-2-yl butyrate to (2R,3E,6R)-6,10-dimethyl-3-undecen-2-ol With Pancreatin from Porcine Pancreas A 1L, three-necked indented flask equipped with mechanical stirrer, a pH electrode and an addition burette filled with 2N NaOH, which was operated by a pH controller and a lab pump, was charged with 113 mL of tap water, 113 mL of pH 8.0, 0.05M phosphate buffer, 3.66 g (6.8 mmol) of sodium taurocholate (from ox bile, crude). The pH was adjusted to 7.5 by addition of a few drops of 85% $H_3PO_4$. Then, 64.1 g of the butyrate, i.e. (2RS,3E,6R)-6,10-dimethyl-3-undecen-2-yl butyrate (0.239 mol, resp. 0.202 mol based on a GC purity of 84.6%) and 4.53 of pancreatin (Grade II, from Porcine pancreas) were added while stirring vigorously. The pH was adjusted to 7.5 by addition of 1.3 mL of 2N NaOH and the hydrolysis was carried out at ambient temperature within a pH range of 7.4–7.6 maintained by automatic addition of 2N NaOH. From the consumption of 0.7 mL of 2N NaOH within the first 15 minutes a specific activity of 21 units/g pancreatin was calculated. After 20.5 hours, at a consumption of 24.5 mL (49 mmol) of 2N NaOH (corresponding to 24% conversion), the reaction was quenched with 300 mL of ethanol. The mixture was stirred for 1 hour, filtered through a Celite pad and the pad was washed with 2×100 mL of ethanol/water, 1:1 parts by volume. The filtrate was poured onto 300 mL of brine and extracted with 3×500 mL of hexane/ether, 1:1 parts by volume. The combined extracts were washed with brine, dried over $Na_2SO_4$, filtered and evaporated to yield 51.4 g of a yellow liquid. Distillation through a 50 cm Goodloe column afforded (a) 20.2 g of alcohol/butyrate mixtures, bp 61°–83° C./0.15 mm; (b) 9.8 g of pure butyrate, bp 82°–86° C./0.1 mm, and (c) 21.2 g of column contents and pot residue. Kugelrohr distillation of this latter material gave another 20.2 g of butyrate. Chromatographic separation of the alcohol/butyrate mixtures on 570 g of silica gel with hexane/ethyl acetate (5%–25%) afforded 11.8 g of (2S,3E,6R)-6,10-dimethyl-3-undecen-2-yl butyrate, and 8.1 g of (2R,3E,6R)-6,10-dimethyl-3-undecen-2-ol. Kugelrohr distillation of this alcohol at ca. 110°–127° C./0.2 mmHg furnished 7.9 g of (2R,3E,6R)-6,10-dimethyl-3-undecen-2-ol as a colorless oil, GC purity 92.75% (16.7% yield, 18.3% chemical yield based on GC purities). The diastereomeric comparison of this alcohol was determined by converting a sample into the butyrate (butyric anhydride, pyridine, 4-dimethylaminopyridine, 20° C., 30 mm) and GC analysis, which showed a (2R,6R)/(2S,6R)diastereomer ratio of 92:8; (84% d.e.).

The combined butyrate fractions from the distillation and the chromatography amounted to 42.8 g, of (2S,3E,6R)-6,10-dimethyl-3-undecen-2-ol GC purity 85% (66.8% recovery; 67% chemical yield based on GC purities).

EXAMPLE 9

Preparation of (2RS,3E,6R)-6,10-Dimethyl-3,9-undecadien-2-ol acetate

A flame-dried, 250 mL, three-necked flask containing a magnetic stirring bar was charged under argon with 7.9 g (8.1 mL, 0.10 mol) of dry pyridine. After cooling in an ice-bath, 10.2 g (9.4 mL, 0.10 mol) of acetic anhydride and then 10.0 g (0.051 mol) of (2RS,3E,6R)-6,10-dimethyl-3,9-undecadien-2-ol were added dropwise, and the reaction was stirred for 2 hours at 0° C. and then overnight at 20° C. The reaction mixture was poured onto 2N HCl/ice and extracted with 2×200 mL of ether. The combined extracts were washed with 2N HCl, sat. NaHCO$_3$ solution, and brine, dried over Na$_2$SO$_4$, filtered and evaporated. Kugelrohr distillation at ca. 105°-130° C./0.1 mmHg afforded 12.05 g (99%) of (2RS,3E,6R)-6,10-dimethyl-3,9-undecadien-2-ol acetate as colorless liquid. Calcd. for C$_{15}$H$_{26}$O$_2$ (238.4): C, 75.58; H, 10.99; Found: C, 75.47; H, 11.04%. $[\alpha]_D^{25} = -2.16°$ (2.04% in CHCl$_3$).

EXAMPLE 10

Preparation (2R,3E,6R)-6,10-Dimethyl-3,9-undecadien-2-ol acetate

A flame-dried 100 mL, three-necked flask with magnetic stirring bar was charged under argon with 2.0 g (10.2 mmol) of (2R,3E,6R)-6,10-dimethyl-3,9-undecadien-2-ol [(2R,6R)/(2S,6R)=90:10 by GC diastereomer analysis of butyrate derivative]. Then, after cooling in an ice-bath, 1.5 g (1.4 mL, 15 mmol) of acetic anhydride, 1.58 g (1.6 mL, 20 mmol) of dry pyridine and 12.3 mg (0.1 mmol) of 4-N,N-dimethylaminopyridine were added, and the reaction was stirred for 75 minutes at ambient temperature. Work-up as described in Example 9 followed by Kugelrohr distillation at ca. 110°/0.25 mm afforded 2.35 g (99%) of (2R,3E,6R)-6,10-dimethyl-3,9-undecadien-2-ol acetate as colorless liquid; GC purity 90%; $[\alpha]_D^{25} = +47.17°$ (5.3% in CHCl$_3$).

EXAMPLE 11

Preparation of (2RS,3E,6R)-6,10-Dimethyl-3-undecen-2-ol Acetate

Acetylation of 5.0 g (25.2 mmol) of (2RS,3E,6R)-6,10-dimethyl-3-undecen-2-ol in the same way as described in Example 10 afforded 5.8 g (96%) of (2RS,3E,6R)-6,10-dimethyl-3-undecen-2-ol acetate, as colorless liquid, GC purity 93%, $[\alpha]_D^{25} = +0.32°$ (5.0% in CHCl$_3$).

EXAMPLE 12

Preparation of (2R,3E,6R)-6,10-Dimethyl-3-undecen-2-ol Acetate

Acetylation of 4.8 g (24.2 mmol) of (2R,3E,6R)-6,10-dimethyl-3-undecen-2-ol (2R,6R/2S,6R 90:10 by GC diastereomer analysis of butyrate derivative) as described in Example 10 afforded 5.7 g (98%) of (2R,3E,6R)-6,10-dimethyl-3-undecen-2-ol acetate as a colorless liquid. $[\alpha]_D^{25} = +50.71°$ (4.9% in CHCl$_3$).

EXAMPLE 13

Preparation (4R,3E,6R)-6,10-Dimethyl-3-undecen-2-yl methyl carbonate

A flame-dried, 100 mL three-necked flask was charged under argon with 3.00 g (15.1 mmol) of (2R,3E,6R)-6,10-dimethyl-3-undecen-2-ol (2R,6R/2S,6R=92:8 by GC diastereomer analysis), 25 mL of dry CH$_2$Cl$_2$, 1.45 g (2.0 mL, 14.3 mmol) of triethylamine and 170 mg (1.4 mmol) of 4-N,N-dimethylaminopyridine. Then, after cooling in an ice-bath, 1.46 g (1.2 mL, 15.4 mmol) of methyl chloroformate was added and the mixture was stirred at ambient temperature. After 17 hours, the mixture was diluted with 20 mL of CH$_2$Cl$_2$ and an additional 8 mL of triethylamine and 4.14 g (43.8 mmol) of methyl chloroformate were added. The reaction was stirred a further 20 hours, after which it still contained much of the substrate alcohol. For the work-up, the mixture was diluted with ether, washed with cold 1N HCl, dil. NaHCO$_3$ solution, and brine, dried over Na$_2$SO$_4$, filtered and evaporated. The yellow oil (3.2 g) obtained, was chromatographed on 150 g of silica gel with hexane/ethyl acetate 1% 5%, and Kugelrohr distilled at ca. 115°-140° C./0.2 mm, to yield 0.70 g (18%) of [(2R,3E,6R)-6,10-dimethyl-3-undecen-2-yl]methyl carbonate calcd: C, 70.27; H, 11.01; Found: C, 70.09; H, 10.83%. $[\alpha]_D^{25} = +41.63°$ (1.2% in CHCl$_3$).

EXAMPLE 14

Preparation of rac.-(6-Benzyloxy-2,5,7,8-tetramethylchroman-2-yl)acetic acid

Esterification of 105.7 g (0.40 mol) of (rac.)-[(6-hydroxy-2,5,7,8-tetramethylchroman-2-yl)]acetic acid with methanol in the presence of p-toluenesulfonic acid according to Cohen et al. *Helv. Chim. Acta.* 1981, 64, 1158 afforded 111.8 g (100%) of the methyl ester as a brown oil which solidified upon standing, mp 65°-64° C. A sample recrystallized from hexane/ethyl acetate showed a mp of 65°-67° C.

Benzylation of 37.85 g (0.135 mol) of this material with benzyl chloride in the presence of K$_2$CO$_3$ afforded 50.6 g (101%) of the benzyl ether ester as a viscous brown resin.

To a solution of 39.7 g (0.107 mol) of the above crude benzyl ether ester in 300 mL of ethanol was added, at ambient temperature, in one portion 15 mL of 40% NaOH (0.15 mol). The mixture was stirred overnight, diluted with 100 mL of water, washed twice with hexane to remove neutral parts and acidified with 2N HCl. The resultant emulsion was extracted with water and brine, dried over Na$_2$SO$_4$, filtered and evaporated. Drying in vacuo afforded 34.6 g (90.5%) of crude acid as a viscous brown oil. Crystallization from 300 mL of ethanol and 100 mL of water afforded 30.4 g (80%) of rac.-(6-Benzyloxy-2,5,7,8-tetramethylchroman-2-yl)acetic acid as a tan solid; mp 107°-113° C. This material was virtually pure by NMR.

EXAMPLE 15

Preparation of rac.-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione Reaction of 17.7 g (50 mmol) of rac.-(6-benzyloxy-2,5,7,8-tetramethylchroman-2-yl)acetic acid with oxalyl chloride according to Cohen et al., *Helv. Chim. Acta.* 1978, 61, 837 afforded 19.9 g (106%) of the acid chloride i.e. rac-(6-benzyloxy-2,5,7,8-tetramethylchroman-2-yl)-acetyl chloride as a very viscous brown oil.

To a solution of 7.46 g (53 mmol) of freshly prepared Meldrum's acid in 30 mL of dry CH$_2$Cl$_2$ (filtered through aluminum oxide) was added under argon, at ca. 5° C. 9.89 g (10.1 mL, 125 mmol) of dry pyridine. To the resulting solution dropwise addition at ca. 5° C. of a solution of 19.8 g of the above acid chloride (ex 49.7 mmol acid) in 30 mL of dry CH$_2$Cl$_2$ was performed over a period of 2 hours. A brown solution containing some white precipitate resulted. After stirring for 1 hour at 0° C. and then for 1 hour at ambient temperature the mixture was poured onto 2N HCL containing crushed ice. The organic layer was separated and washed twice with 2N HCl and twice with brine, then dried over Na$_2$SO$_4$, filtered, evaporated and dried in vacuo to leave 24.5 g of crude adduct as a brown resin. This material was dissolved in ca. 70 mL of CH$_2$Cl$_2$ and the total volume was adjusted to 100 mL with CH$_2$Cl$_2$. An aliquot of 20 mL of this solution was evaporated and the residue was dissolved in 25 mL of hot diisopropyl ether and 5 mL of hexane. The hot solution was filtered to remove some dark-brown particles and then allowed to cool overnight. The precipitated crystals were collected by filtration, washed with hexane and dried in vacuo to afford 3.55 g (73%) of rac.-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione as a tan powder, mp 94.5°-96° C. (dec.).

EXAMPLE 16

Preparation of rac-3-Oxo-4-[3,4-dihydro-2,5,7,8-tetramethyl-6-(phenylmethoxy)-2H-1-benzopyran-2-yl]butanoic acid methyl ester The remaining aliquot of 80 mL of the solution of rac.-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione was evaporated and the residue was dissolved in 20 ml of benzene and 120 mL of methanol. The solution was heated to reflux for 4 hours, cooled and evaporated to leave a brown oil. A solution of this material in 100 mL of ether was washed with sat. NaHCO$_3$ solution, water and brine, dried over Na$_2$SO$_4$, filtered and evaporated. The residue (16.9 g of a brownish oil) was chromatographed on silica gel (500 g, hexane/ethyl acetate 15%–25%) to afford, after drying in vacuo, 14.1 g (86%) of rac-3-oxo-4[3,4-dihydro-2,5,7,8-tetramethyl-6-(phenylmethoxy)-2H-1-benzopyran-2-yl]butanoic acid methyl ester as a pale yellow, viscous oil. After standing for some time, this material solidified. A sample was recrystallized from hexane at 0° C. to afford pale yellow crystals, mp 68.5°-70° C.

EXAMPLE 17

Preparation of (S)-(6-benzyloxy-2,5,7,8-tetramethylchroman-2-yl)acetic Acid

To a solution of 18.5 g (50 mmol) of methyl (S)-(6-benzyloxy-2,5,7,8-tetramethyl-chroman-2-yl)acetate in 475 mL of methanol and 10 mL of ether was added, at 10° C., 50 mL of 2N NaOH and the milky mixture was stirred at ambient temperature for 16 hours. Since at that point the hydrolysis was far from being complete, an additional 50 mL of 2N NaOH and 100 mL of methanol were added and the resulting clear solution was stirred for a further 8 hours. The solution was extracted twice with hexane/ether, 2:1 parts by bolume to remove the remaining unreacted ester, then it was acidified with 2N HCl and extracted 5 times with hexane/ether, 1:1 parts by volume. The combined extracts were washed with water and brine, dried over Na$_2$SO$_4$, filtered and evaporated to afford 16.05 g (90.5%) of S-(6-benzyloxy-2,5,7,8-tetramethyl chroman-2-yl)acetic acid as a white foam; $[\alpha]_D^{25} = -9.88°$ (1.5% in ethanol) (1.47% in ethanol)]. Crystallization from hexane afforded in two crops 14.54 g (82%) of (S)-(6-benzyloxy-2,5,7,8-tetramethylchroman-2-yl)acetic acid as white crystals, mp 91°-96° C.; $[\alpha]_D^{25} = -10.36°$ (1.32% in ethanol). The observed specific rotations indicate an optical purity of 93–95% for this product.

EXAMPLE 18

Preparation of (S)-3-Oxo-4-[3,4-dihydro-2,5,7,8-tetramethyl-6-(phenylmethoxy)-2H-1-benzopyran-2-yl]butanoic acid methyl ester Reaction of 11.8 g (33.3 mmol) of (S)-(6-bezyloxy-2,5,7,8-tetramethylchroman-2-yl)acetic acid with oxalyl chloride according to Cohen et al *Helv. Chim. Acta*, 1978 61, 837 afforded 13.0 g (105%) of (S)-(6-benzyloxy-2,5,7,8-tetramethylchroman-2-yl)acetyl chloride as a yellow oil. This acid chloride was reacted according to Org. Synth., 1984, 63, 198 with 4.94 g (34.3 mmol) of Meldrum's acid and 6.58 g (6.73 mL, 83.2 mmol) of dry pyridine as described above for the racemic series to afford 16.5 g of crude adduct i.e.(S)-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione as a brownish foam. Crystallization attempts from several solvents or solvent mixtures failed.

The crude adduct prepared above was dissolved in 20 mL of benzene and 100 mL of methanol, and the solution was refluxed for 2 hours and stirred overnight at ambient temperature. Evaporation afforded 13.8 g of a yellow oil, which was chromatographed on silica gel (250 g, hexane/20% ethyl acetate) to yield 11.5 g (84%) of (S)-3-oxo-4-[-3,4-dihydro-2,5,7,8-tetramethyl-6-(phenylmethoxy)-2H-1-benzopyran-2-yl]butanoic acid methyl ester. Rechromatography on silica gel (500 g, hexane/15% ethyl acetate) afforded 9.30 g (68%) of this keto ester as a colorless resin which slowly crystallized. $[\alpha]_D^{25} = +14.2°$ (2.7% in CHCl$_3$).

EXAMPLE 19

Preparation of (S)-3-Oxo-4-[3,4-dihydro-2,5,7,8-tetramethyl-6-(phenylmethoxy)-2H-1-benzopyran-2-yl]butanoic acid benzyl ester A solution of 31.0 g of crude Meldrum's acid adduct (S)-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione and 7.52 g (69.5 mmol) of benzyl alcohol in 100 mL of dry toluene was heated under argon to 110° C. Carbon dioxide evolution started at ca. 100° C. and ceased after ca. 1 hour. The brown solution was heated a further 3 hours at 110° C. The cooled solution was diluted with hexane, washed successively with sat. NH$_4$Cl solution, water, sat. NaHCO$_3$ solution and brine, dried over Na$_2$SO$_4$, filtered, evaporated and dried in vacuo overnight to leave 32.9 g of a yellow-brown solid. Attempted crystallization from a mixture of 200 mL of hexane/40 mL of ether/20 mL of ethyl acetate afforded a white crystalline material accompanied by some brown solid material, which had initially precipitated as an oil. The mixture was evaporated and the brown residue was filtered through a short column of silica gel (500 g, hexane/ethyl acetate 7%–15%) to afford 25.6 g (83%) of (S)-3-oxo-4-[3,4-dihydro-2,5,7,8-tetramethyl-6-(phenylmethoxy)-2H-1-benzopyran-2-yl]butanoic acid benzyl ester as a white solid. Recrystallization from a mixture of 200 mL of hexane/40 mL of ether/10 mL of ethyl acetate at −5° C. afforded 21.0 g (68%) of this product as fine white needles, mp 72.5°–74° C. (sintered from 65° C.). From the mother liquor another 1.60 g of white crystals of this product were obtained, mp 72°–74° C.; combined yield 22.60 g (73.5%), $[\alpha]_D^{25} = +16.11°$ (2.46% in CHCl$_3$).

EXAMPLE 20

A. Pd-Catalyzed Coupling Reactions: General Procedure

Unless otherwise noted, the coupling reactions, in Example 20 were carried out according to the following procedure: An oven-dried 50 mL Schlenk tube equipped with a magnetic stirring bar and capped with a rubber septum was charged under argon with 240–480 mg (5–10 mmol) of 50% NaH dispersion in mineral oil. The mineral oil was removed by 3 cycles of suspending the NaH in a 3–5 mL of hexane, stirring for a short period of time, allowing the solid to settle and removing the supernatant liquid via syringe. After drying the NaH for 5–10 minutes in vacuo, 5–10 mL of dry THF (distilled from sodium/benzophenone ketyl under argon) was injected via syringe. To the resulting suspension, at 0°–5° C. was added, dropwise, the solution of 5–11 mmol of the starting keto ester in 10–25 mL of dry THF via syringe at such a rate as to control the evolution of hydrogen. This keto ester solution had been prepared previously under argon in another dry Schlenk tube. The mixture was stirred at ambient temperature until the gas evolution ceased, and after this it was allowed to stand for 30–60 minutes. Some dark particles settled to the bottom of the flask leaving a yellow brownish clear supernatant liquid.

In the meantime, an oven-dried 100–250 mL Schlenk flask containing a magnetic stirring bar was charged in the dry-box with ca. 0.25–0.5 mmol (ca. 5 mol%) of tetrakis(triphenylphosphine)palladium(O). To this vessel at 0° C. a solution of 5–10 mmol of the C$_{13}$ alcohol derivative starting material in 10–20 mL of dry THF, (which had been previously prepared under argon in another Schlenk tube) was added via syringe. The ice-bath was removed and the resulting yellow suspension was stirred for 5–10 minutes. Then the above prepared solution of the sodium salt of the β-keto ester was added rapidly via syringe. A clear greenish-yellow solution resulted which was stirred at ambient temperature for 26–120 hours. Samples of the reaction mixture were periodically taken via syringe and analyzed by TLC to monitor the progress of the reaction. For the work-up the greenish-yellow sometimes slightly opaque solution was diluted with hexane and washed with sat. NH$_4$Cl solution, sat. NaHCO$_3$ solution and brine, filtered to remove some yellow precipitate, dried over Na$_2$SO$_4$, filtered and evaporated. The dark-yellow oil obtained was then chromatographed on silica gel and the keto-ester thus isolated was dried in vacuo to constant weight.

B.
(2RS,4′RS,8′R)-6-Benzyloxy-2-(3′-carbomethoxy-2′-oxo-4′,8′,12′-trimethyl-5′,11′-tridecadienyl)-2,5,7,8-tetramethylchroman Deprotonation of 2.05 g (5.0 mmol) of rac.-3-oxo-4-[3,4-dihydro-2,5,7,8-tetramehtyl-6(phenylmethoxy) 2H-1-benzopyran-2-yl]butanoic acid methyl ester with 240 mg (5.0 L mmol) of 50% NaH dispersion was carried out as described in Pd-Catalyzed Coupling Reactions General Procedure in 20 mL of THF. The resulting mixture, which still contained some unreacted NaH particles, was added to a mixture of 1.192 g (5.0 mmol) of (2RS,3E,6R)-6,10-dimethyl-3,9-undecandien-2-ol acetate (GC purity 87%) and 428 mg (0.37 mmol, 7.4 mol%) of Pd(PPh$_3$)$_4$ in 5 mL of THF. The reaction mixture was stirred for 2 hours at ambient temperature and for 14 hours at 50° C. Chromatography (200 g silica gel, hexane/ethyl acetate 3%–7.5%) afforded 1.95 g (66%) of the mono-alkylation product (2RS,4′RS,8′R)-6-benzyloxy-2-(3′-carbomethoxy-2′-oxo-4′,8′,12′-trimethyl-5′,11′-tridecadienyl)-2,5,7,8-tetramethylchroman as a colorless oil. NMR- and HPLC analyses indicated this latter material to be a 1:1:1:1 mixture of 4-diastereomers.

C.
(2S,4′R,8′R)-6-Benzyloxy-2-(3′-carbomethoxy-2′-oxo-4′,8′,12′-trimethyl-5′,11′-tridecadienyl)-2,5,7,8-tetramethylchroman The sodium salt of (S)-keto ester prepared from 4.105 g (10.0 mmol) of (S)-3-oxo-4-[3,4-dihydro-2,5,7,8-tetramethyl(phenylmethoxy)-2H-1-benzopyran-2-yl]butanoic acid methyl ester (92% e.e.) and 432 mg (9.0 mmol) of 50% NaH dispersion in 30 mL of THF was reacted with a mixture of 2.135 g (8.95 mmol) of (2R,3E,6R)-6,10-dimethyl-3,9-undecadien-2-ol acetate (diastereomer ratio 2R,6R/2S,6R=90:10; gross GC purity 90%) and 608 mg (0.526 mmol, 5.8 mol% Pd(PPh$_3$)$_4$ in 20 mL of THF for 26 hours at ambient temperature. This reaction afforded, after chromatography (300 g silica gel, hexane/ethyl acetate 3.5%–6%), 4.30 g (81.5%) of (2S,4′R,8′R)-6-benzyloxy-2-(3′-carbomethoxy-2′-oxo-4′,8′, 12′-trimethyl-5′,11′-tridecadienyl)-2,5,7,8-tetramethylchroman as a colorless viscous oil. NMR analysis (200 MHz, C$_6$D$_6$) indicated a diastereomer composition of 1:2:2:1. HPLC analysis showed a diastereomer ratio of 17:32:18:33, thus indicating a 4′R/S ratio of 65:35. Calcd for C$_{38}$H$_{52}$O$_5$ (588.84): C, 77.51; H, 8.90; Found: C, 77.56; H, 8.92%.

D.
(2RS,4′RS,8′R)-6-Benzyloxy-2-(3′-carbomethoxy-2′-oxo-4′,8′,12′-trimethyl-5′-tridecenyl)-2,5,7,8-tetramethylchroman (1) A solution of the sodium salt of keto ester, i.e. rac.-3-oxo-4-[3,4-dihydro-2,5,7,8-tetramethyl-6-(phenylmethoxy)-2H-1-benzopyran-2-yl]butanoic acid methyl ester, prepared from 4.516 g (11.0 mmol) of the keto ester and 490 mg (10 mmol) of 50% NaH dispersion in 30 mL of THF, was reacted with 2.404 g (100 mmol) of (2RS,3E,6R)-6,10-dimethyl-3-undecen-2-yl acetate, (GC purity 93%) and 560 mg (0.484 mmol, 4.8 mol%) of Pd(PPh$_3$)$_4$ in 10 mL of THF for 70 hours at ambient temperature. Chromatography (200 g silica gel, hexane/ethyl acetate 2.5%–5%) afforded 78 mg (1%) of a presumable dialkylation product and 5.80 g (98%) of (2RS,4′RS,8′R)-6-benzyloxy-2-(3′-carbomethoxy-2′-oxo-4′,8′,12′-trimethyl-5′-tridecenyl)-2,5,7,8-tetramethylchroman as a colorless viscous oil. NMR and HPLC analyses indicated a 1:1:1:1 diastereomeric mixture. Calcd for C$_{38}$H$_{54}$O$_5$ (590.85): C, 77.25; H, 9.21; Found: C, 76.57; H, 9.26%.

(2) As set forth in part 1 of this example, the sodium salt of the acetate, i.e. racemic keto ester was reacted with the acetate i.e. (2RS,3E,6R)-6,10-dimethyl-3-undecen-2-yl acetate except that a mixture of 57.5 mg (0.10 mol%) of bis(dibenzylidene acetone)palladium (0) and 40 mg (0.10 mmol, 2 mol%) of 1,2-bis-(diphenylphosphino)ethane in 15 ml of THF was used as the catalyst. The coupling product produced was (2RS,4′RS,8′R)-6-benzyloxy-2-(3′-carbomethoxy-2′-oxo-4′,8′,12′-trimethyl-5′-tridecenyl-2,5,7,8-tetramethyl chroman. According to TLC analyses the alkylation apparently stopped after ca. 48 hours with some acetate (2RS,6R) remaining unconsumed. Chromatography (200 g silica gel, hexane/ethyl acetate 3%→5%) afforded 244 mg (20% recovery) of acetate (2RS,6R) and 2.310 g (78%) of coupling product, i.e. the (2RS,4′RS,8′R) isomer, as colorless viscous oil. NMR analysis and decoupling experiments indicated a 1:1:1:1 diastereomeric mixture and trans configuration at the double bond for all 4 diastereomers. Calcd. for $C_{38}H_{54}O_5$ (590.85): C, 77.25; H, 9.21. Found: C, 77.56; H, 9.50%.

E. (2S,4′RS,8′R)-6-Benzyloxy-2-(3′-carbomethoxy-2′-oxo-4′,8′,12′-trimethyl-5′-tridecenyl)-2,5,7,8-tetramethylchroman A solution of the sodium salt of keto ester (S)-3-oxo-4-[dihydro-2,5,7,8-tetramethyl-6-(phenylmethoxy)-2H-1-benzopyran-2-yl]butanoic acid methyl ester prepared from 2.46 g (6.0 mmol) of the keto ester (92% ee) and 240 mg (5.0 mmol) of 50% NaH dispersion in 25 mL of THF was reacted with a mixture of 1.202 g (5.0 mmol) of the acetate i.e. (2RS,3E,6R)-6,10-dimethyl-3-undecen-2-yl acetate (GC purity 93%) and 246 mg (0.213 mmol, 4.2 mol%) of Pd(PPh₃)₄ in 10 mL of THF at ambient temperature for 26 hours. Chromatography (300 g silica gel, hexane/ethyl acetate 3%→10%) afforded 769 mg of (2S,4′RS,8′R)-6-benzyloxy-2-(3′-carbomethoxy-2′-oxo-4′,8′,12′-trimethyl-5′-tridecenyl)-2,5,7,8-tetramethylchroman (diastereomeric ratio 1:20:6:5 by NMR) and 2.45 g of (2S,4′RS,,8′R)-6-benzyloxy-2-(3′-carbomethoxy-2′-oxo-4′,8′,12′-trimethyl-5′-tridecenyl)-2,5,7,8-tetramethylchroman (1:1:1:1 diastereomeric ratio by NMR); combined yield 2.62 g (88.5%). Calcd fo $C_{38}H_{54}O_5$ (590.85): C, 77.25; H, 9.21; Found: C, 77.09; H, 9.29%.

From the more polar fractions of the chromatography, 0.70 g of keto ester (S)-3-oxo-4-[3,4-dihydro-2,5,7,8-tetramethyl-β-oxo-6-(phenylmethoxy)-2H-1-benzopyran-2-yl]butanoic acid methyl ester were isolated as semi-solid material. $[\alpha]_D^{25} = +14.72°$ (2.8% in CHCl₃). This amounts to a 28% recovery of this keto ester which had been used in 20% excess.

F. Optically Active Series: (2S,4′R,8′R)-6-Benzyloxy-2-(3′-carbomethoxy-2′-oxo-4′,8′,12′-trimethyl-5′-tridecenyl)-2,5,7,8-tetramethylchroman A solution of the sodium salt of keto ester i.e. (S)-3-oxo-4[dihydro-2,5,7,8-tetramethyl-6-(phenylmethoxy)-2H-1-benzopyran-2-yl]butanoic acid methyl ester prepared from 881 mg (2.146 mmol) of the keto methyl ester (ca. 98% ee) and 98.2 mg (2.05 mmol) of 50% NaH dispersion in 13 mL of THF was added to a mixture of 500 mg (1.95 mmol) of (2R,3E,6R)-6,10-dimethyl-3-undecen-2-yl methyl carbonate (diastereomer ratio 2R,6R/2S,6R=90:10) and 113 mg (0.098 mmol, 5 mol%) of Pd(PPh₃)₄ in 5 mL of THF. Immediate gas evolution occurred, which ceased after a few minutes. The mixture was stirred for 18 hours at ambient temperature. Chromatography (75 g silica gel, heptane/ethyl acetate 5%→10%) afforded 1.036 g (90%) of (2S,4′R,8′R)-6-benzyloxy-2-(3′-carbomethoxy-2′-oxo-4′,8′,12′-trimethyl-5′-tridecenyl)-2,5,7,8-tetramethylchroman as a colorless oil. NMR analysis (200 MHz, C₆D₆) indicated a 1:6:6:1 diastereomeric ratio. HPLC analyses showed a 8:42:43:7 mixture of 4 diastereomers, which indicates a 4′R/S ratio of 85:15.

EXAMPLE 21

(2S,2′RS,4′R,8′R)-6-Benzyloxy-2-(3′carbomethoxy-2′-hydroxy-4′,8′12′-trimethyl-5′,11′-tridecadienyl)-2,5,7,8-tetramethylchroman To a solution of 2.10 g (3.566 mmol) of keto ester (2S,4′R,8′R)rac-6-benzyloxy-2-(3′-carbomethoxy-2′-oxo-4′,8′,12′-trimethyl-5′,11′-tridecadienyl)-2,5,7,8-tetramethylchroman in 5 mL of THF and 25 mL of methanol at 0° C., 400 mg (10.6 mmol) of NaBH₄ was added over a period of 2 hours, in several small portions.

After stirring for a further 2 hours at ambient temperature, the reaction was quenched by dropwise addition of 2N HCl. The mixture was diluted with hexane and washed with 2N HCl, sat. NaHCO₃ solution and brine, dried over Na₂SO₄, filtered and evaporated to afford 1.80 g (85.5%) of crude (2S,2′RS,4′R,8′R)-6-benzyloxy-2-(3′carbomethoxy-2′-hydroxy-4′,8′12′-trimethyl-5′,11′-tridecadienyl)-2,5,7,8-tetramethylchroman as a colorless resin.

EXAMPLE 22

(2S,2′RS,4′R,8′R)-6-Benzyloxy-2-(3′-carboxy-2′-hydroxy-4′,8′,12′-trimethyl-5′,11′-tridecadienyl)-2,5,7,8-tetramethylchroman A mixture of 1.80 g (3.046 mmol) of the crude hydroxy ester, from Example 21, 10 mL of THF, 40 mL of ethanol and 4 mL of 15% NaOH was heated under argon to reflux for 3 hours. A dark-brown solution formed. The cold mixture was diluted with ethanol and the solution was washed with hexane to remove neutral parts, then acidified with 2N HCl and extracted twice with hexane/ether, 1:1 parts by volume. The combined extracts were washed with brine, dried over Na₂SO₄, filtered, evaporated and dried in vacuo to afford 1.52 g (86.5%) of crude hydroxy acid [title compound] as a brown resin.

EXAMPLE 23

Benzyl Ether of (2S,4′R,8′R)-2′,5′,11′-α-Tocotrienol

To a solution of 1.52 g (2.63 mmol) of crude hydroxy acid from Example 22 in 10 mL of dry toluene under argon at 0° was added 730 mg (881 μl, 3.156 mmol) of DMF dineopentyl acetal (redistilled) via syringe. The yellow-brown solution was stirred for 2 hours at ambient temperature and then for 1.5 hours at 50° C. The cool solution was diluted with hexane, washed with 2N HCl, sat. NaHCO₃ solution and brine, dried over Na₂SO₄, filtered and evaporated to leave 1.6 g of a brown oil. Chromatography on 200 g silica gel (hexane/ethyl acetate 0.5%–2.5%) afforded 839 mg (62%) of the benzyl ether of (2S,4′R,8′R)-2′,5′,11′-α-tocotrienol as a colorless oil.

EXAMPLE 24

(2R,4′R,8′R)-α-Tocopherol

A solution of 420 mg (0.816 mmol) of the benzyl ether triene from Example 23 in 5 mL of THF and 20 mL of ethanol was hydrogenated for 4 hours at 20 psi H₂ over ca. 1 g of Raney nickel (washed 3 times with ethanol). The mixture was filtered and evaporated. The residue was dissolved in hexane/ether, 1:1 parts by volume and the solution was washed with 2N HCl, sat. NaHCO$_3$ solution and brine, dried over Na$_2$SO$_4$, filtered and evaporated to afford 360 mg. (102%) of α-tocopherol as a colorless oil. According to the NMR, this material still contained about 20% of olefins. Therefore, it was subjected again to an analogous hydrogenation carried out at 50 psi for 6 hours. Work-up as described above afforded 362 mg (103%) of α-tocopherol as a colorless oil which, according to the NMR, still contained ca. 7% of olefinic material.

An aliquot of 280 mg (0.653 mmol) of this product was hydrogenated over 50 mg of PtO$_2$ in 20 mL of ethyl acetate at 50 psi H$_2$ pressure for 1 hour. Work-up as described above followed by chromatography on 50 g of silica gel (hexane/5% ethyl acetate) afforded 240 mg (85%) of (2R,4'R,8'R)α-tocopherol as a pale yellow oil. No olefinic protons were discernible in its NMR spectrum.

EXAMPLE 25

Preparation of (2RS)-3-Oxo-4-[3,4-dihydro-2,5,7,8-tetramethyl-6-(phenylmethoxy)-2H-1-benzopyran-2-yl]butanoic acid (1RS,2E,5R)-1,5,9-trimethyl-2-decenyl ester A solution of 2.40 g (5.0 mmol) of Meldrum's acid adduct i.e. rac.-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione and 1.19 g (6.0 mmol) of alcohol (2RS,3E,6R)-6,10-dimethyl-3-undecen-2-ol in 4 mL of dry toluene was degassed by 3 cycles of evacuating/purging with argon and then heated under argon to 100° C. CO$_2$ evolution started at ca 90° C. and ceased after ca. 30 minutes. The light yellow solution was stirred for another 2 hours at 100° C. The cooled solution was diluted with hexane, washed with water, sat. NaHCO$_3$ solution and brine, dried over Na$_2$SO$_4$, filtered and evaporated to leave 3.6 g of a brown oil. Chromatography on 250 g of silica gel (hexane/ethyl acetate 5%–6%) afforded 2.33 g (81%) of [2R,S)-3-oxo-4-[3,4-dihydro-2,5,7,8-tetramethylβ-oxo-6-(phenylmethoxy)-2H-1-benzopyran-2-yl-butanoic acid-1,5,9-trimethyl-2-decenyl ester as a colorless very viscous oil.

EXAMPLE 26

Preparation of (2S)-3-oxo-4-[3,4-dihydro-2,5,7,8-tetramethyl-6-(phenylmethoxy)-2H-1-benzopyran-2-yl]butanoic acid (1R,2E,5R)-1,5,9-trimethyl-2-decenyl ester By an analogous reaction to Example 25, utilizing 7.35 g (14.96 mmol) of Meldrum's acid adduct i.e. (S)-5-[2-[3,4-dihydro-2,5,7,8-tetramethyl-6-phenylmethoxy-2H-1-benzopyran-2-yl]-1-hydroxyethylidene]-2,2-dimethyl-1,3-dioxane-4,6-dione (ca. 98% ee) with 2.967 g (14.96 mmol) of (2R,3E,6R)-6,10-dimethyl-3-undecen-2-ol (GC purity 91%, diastereomer ratio 2R,6R/2S,6R=90:10) afforded, after chromatography, 7.40 g (85.7%) of (2S)-3-oxo-4-[3,4-dihydro-2,5,7,8-tetramethyl-6-(phenylmethoxy)-2H-1-benzopyran-2-yl]butanoic acid (1R,2E,5R)-1,5,9-trimethyl-2-decenyl ester as a colorless viscous oil.

EXAMPLE 27

Preparation of (2S,4'RS,8'R)-1-[3,4-dihydro-2,5,7,8-tetramethyl-6-[phenylmethoxy]-2H-1-benzopyran-2-yl]-4',8',12'-trimethyl-5'-tridecen-2'-one A dry 50 mL Schlenk tube was charged under argon with 1.75 g (3.034 mmol) of (2S)-3-oxo-4-[3,4-dihydro-2,5,7,8-tetramethyl-6-(phenylmethoxy)-2H-1-benzopyran-2-yl]butanoic acid (1RS,2E,5R)-1,5,9-trimethyl-2-decenyl ester and 5 mL of dry DMF. The solution was deoxygenated by 3 cycles of evacuating/purging with argon. Then, at 0° C., 128 mg (0.11 mmol, 3.6 mol%) of Pd(PPh$_3$)$_4$ was added in one portion and the mixture was again deoxygenated. After 1 hour of stirring at ambient temperature only little of the catalyst had dissolved. Therefore, 5 mL of THF were added as a cosolvent. A clear yellow solution resulted which was stirred for 20 hours at ambient temperature. The solution was diluted with hexane and a sat. NH$_4$Cl solution, and the mixture was filtered through Celite to remove some precipitated yellow solid. The organic layer was separated, washed with dilute NH$_4$OAc solution, sat. NaHCO$_3$ solution and brine, dried over Na$_2$SO$_4$, filtered and evaporated. Chromatographic separation on 150 g of silica gel (hexane/ethyl acetate 2%–5%) afforded 7.280 g (79%) of (2S,4'RS,8'R)-1-[3,4-dihydro-2,5,7,8-tetramethyl-6-[phenylmethoxy]-2H-1-benzopyran-2-yl]-4',8',12'-trimethyl-5'-tridecen-2'-one as a colorless oil. Calcd for C$_{36}$H$_{52}$O$_3$ (532.81): C, 81.15; H, 9.84; Found: C, 80.91; H, 10.01%.

EXAMPLE 28

An analogous reaction to Example 27 was carried out utilizing (2S)-3-oxo-4-[3,4-dihydro-2,5,7,8-tetramethyl-6-(phenylmethoxy)-2H-1-benzopyran-2-yl]butanoic acid (1R,2E,5R)-1,5,9-trimethyl-2-decenyl ester (0.950 g 1.647 mmol) and 995 mg (0.0822 mmol) of Pd(PPh$_3$)$_4$ in 10 mL of dry toluene for 18 hours at 50° C. This reaction afforded 0.95 g of a yellow oil containing (2S,4'R,8'R)-1-[3,4-dihydro-2,5,7,8-tetramethyl-6-[phenylmethoxy]-2H-1-benzopyran-2-yl]-4',8',12'-trimethyl-5'-tridecen-2'-one. HPLC analysis of this crude mixture showed an 89:11 diastereomer ratio for the extrusion product. Chromatographic separation on 100 g silica gel (hexane/ethyl acetate, 2%–5%) afforded 317 mg (36%) of (2S,4'R,8'R)-1-[3,4-dihydro-2,5,7,8-tetramethyl-6-[phenylmethoxy]-2H-1-benzopyran-2-yl]-4',8',12'-trimethyl-5'-tridecen-2'-one as a colorless oil.

EXAMPLE 29

Preparation of (2R,6R,3E)-6,10-Dimethyl-2-hydroxy-3,9-undecadiene

A 3 L, three-necked flask was fitted with a mechanical stirrer and a pH electrode which automatically delivered 4N aqueous NaOH solution from a reservoir. The flask was charged with 1170 mL of pH 8 buffer solution (0.05M monobasic potassium phosphate/NaOH), 280.5 g (0.958 mole) of the butyrate which is (2RS,3E,6R)-6,10-Dimethyl-3,9-undecadien-2-yl butyrate, (91.0% chemical purity by GC analysis). Stirring was started and the pH of the mixture was adjusted to 7.5 by dropwise addition of sufficient 85% phosphoric acid. Then 7.6 g of Triton X-100 was added, followed by 12.1 g of lipase from a Pseudomonas sp. (Lipase P Amano,).

The pH of the reaction mixture was maintained between 7.4 and 7.6 by automatic addition of the 4N NaOH solution. Based on the rate of addition, the enzyme activity at t=15 minutes was calculated to be 67.2 μmol/min/gram of enzyme.

At 46.6% conversion, based on the consumption of 111.6 mL of 4N NaOH solution, the reaction was quenched by addition of 1300 mL of 2B ethanol. The mixture was allowed to stir over a weekend.

The mixture was then filtered through a pad of Celite and the solid washed with 3×500 mL of 1:1 ether/hexane mixture. The filtrate and washing mixture was divided into two portions and each, separately, was treated with 200 mL of brine and extracted with 3×1 L of 1:1 ether/hexane mixture. The combined organic layers were dried over $Na_2SO_4$ and stripped of solvent under reduced pressure to give 254.8 g of a cloudy yellow liquid. This liquid contained the alcohol (2R,6R,3E)-6,10-Dimethyl-2-hydroxy-3,9-undecadiene and butyrate (2S,6R,3E)-6,10-dimethyl-3,9-undecadien-2-ol butyrate. This crude alcohol/butyrate mixture was vacuum distilled through a 30 cm Goodloe column to give (2R,6R,3E)-6,10-dimethyl-2-hydroxy-3,9-undecadiene in the following fractions:

| fraction # | temp(°C.) | press (mmHg) | wt. (g) | GC purity & alcohol/butyrate ratio | appearance |
| --- | --- | --- | --- | --- | --- |
| 1 | 77–9 | 0.05 | 1.8 | 58.6/0.0 | colorless |
| 2 | 73–75 | 0.075 | 4.4 | 68.3/0.0 | colorless |
| 3 | 76 | 0.05 | 45.3 | 92.2/0.0 | colorless |
| 4 | 77 | 0.075 | 42.9 | 92.3/0.0 | colorless |
| 5 | 78–91 | 0.1 | 47.7 | 8.7/83.5 | light yellow |
| 6 | 94–6 | 0.05–.01 | 31.8 | 0.0/92.6 | light yellow |
| 7 | 91–4 | 0.1 | 15.7 | 0.0/94.1 | light yellow |
| 8 (pot) | — | — | ~52.4 | — | yellow |

After the distillation, some material rinsed out of the column with hexane was combined with the pot residue as recyclable butyrate.

The alcohol which is (2R,6R,3E)-6,10-dimethyl-2-hydroxy-3,9-undecadiene contained in fraction 5 was isolated by chromatography on silica gel (543 g of 70–230 mesh) using initially 2% ethyl acetate in hexane as eluent. In this manner 40.8 of the butyrate with a purity of 90.0% was recovered from distillation fraction 5. By eluting with 25% ethyl acetate in hexane, 5.0 g (Kugelrohr distilled) of 100% pure alcohol was recovered from distillation fraction 5.

The total isolated yields of the alcohol and butyrate were 46.0% and 46.9% respectively, based on GC chemical purity of the various fractions.

The diastereomeric excess of the alcohol obtained was 95.8%. The disatereomeric excess of the butyrate obtained was 93.8%.

EXAMPLE 30

Preparation of Methyl(2R,6R,3E)-6,10-Dimethyl-3,9-undecadien-2-yl Carbonate

A flame-dried, argon-filled, 5 L three-necked Morton flask was set up with a mechanical stirrer and dry ice/acetone cooling bath. The flask was charged with 279.2 g (1.33 mole) of (2R,6R,3E)-6,10-dimethyl-2-hydroxy-3,9-undecadiene having a chemical purity of 93.8% and a diastereomeric excess of ~95%. To this was added 500 mL of dry THF via syringe. An addition funnel mounted on the flask was charged via cannula with 860 mL (1.33 mole) of n-butyl lithium (1.55M in hexane solution). After chilling the flask contents in the dry ice/acetone bath for 10 minutes, dropwise addition of the n-butyl lithium was started, and completed during 80 minutes. The addition funnel was rinsed into the flask with 1×50 mL and 1×30 mL of dry THF. The funnel was then charged with 114.4 mL (139.9 g, 1.48 mole) of distilled methyl chloroformate (97%). Thirty minutes after the n-butyl lithium addition was completed, dropwise addition of the methyl chloroformate was started. After this addition was complete, the cooling bath was removed and the mixture was stirred overnight under argon and at room temperature. By TLC analysis the reaction was complete.

The reaction mixture was poured in four portions into a separatory funnel containing 1400 mL of saturated $NH_4Cl$ solution, with shaking between each addition. The reaction flask was rinsed into the funnel with 500 mL of water and 600 mL of ether. After thoroughly shaking the mixture, the organic layer was removed and combined with 2×600 mL ether extracts of the aqueous layer. The combined organic material was washed with 1 L of water, dried over 550 g of $Na_2SO_4$, filtered and stripped of solvent on the rotovapor, finally under a vacuum less than 1 mm Hg. The crude carbonate so obtained weighed 381 g.

This material was chromatographed in two portions on a total of 8 kg of silica gel using first 2% by volume ethyl acetate in 98% by volume hexane and then 4% by volume ethyl acetate in 96% by volume hexane as the eluent. The columns were run at a flow rate of 150–200 mL/minute and 450 mL fractions were collected. The elution of product was monitored by TLC. The fractions containing pure carbonate were combined and stripped of solvent under high vacuum to give, altogether, 342.1 g (101% yield) of methyl (2R,6R,3E)-6,10-dimethyl-3,9-undecadien-2-yl carbonate as a colorless liquid.

EXAMPLE 31

Preparation of (S)-(6-Benzyloxy-2,5,7,8-tetramethylchroman-2-yl) Acetic Acid Chloride 201.0 g (0.57 mole) of (S)-(6-benzyloxy-2,5,7,8-tetramethylchroman-2-yl)acetic acid was dissolved in 1.0 L toluene and transferred to a 3 L three necked flask equipped with a Dean-Stark trap and condenser, magnetic stirrer and a thermometer connected to a heating mantle. The solution was refluxed 1 hour with no appreciable amount of water collecting in the Dean-Stark trap. This was removed, and the solution was cooled to 50° C. Then a pressure equalizing addition funnel was placed on top and the oxalyl chloride 58.5 mL (0.68 mole, 1.2 equiv.) was added dropwise at about one drop per second. The color became orange, and the temperature increased to about 60° C. as gas evolution began smoothly. The rate of addition was monitored so that gas evolution was not too vigorous. The gas evolved was bubbled through two aqueous sodium hydroxide traps. The slow addition was continued over about 1 hour and then heating was applied with a thermowatch keeping the heat at 60° C. The solution was then condensed on the rotovap, and after pumping off any residual solvent for 2 hours, 215.2 g (>100%) of (S)-(6-benzyloxy-2,5,7,8-tetramethyl chroman-2-yl)acetic acid chloride was obtained (211.45 g theoretical).

EXAMPLE 32

(S)-3-Oxo-4-[3,4-dihydro-2,5,7,8-tetramethyl-6-(phenylmethoxy)-2H-1-benzopyran-2yl]-butanoic Acid Methyl Ester 211.4 g (0.57 mole) of (S)-(6-benzyloxy-2,5,7,8-tetramethylchroman-2-yl)acetic acid chloride was dissolved in 250 mL of $CH_2Cl_2$ and placed in a 1000 mL pressure equalizing addition funnel. 89.9 g (0.62 mole, 1.1 equiv.) of Meldrum's acid was dissolved in 200 mL of dichloromethane. Because of some insoluble material present the solution was passed through a fritted funnel and 0.1 equiv. (8 g) of additional Meldrum's acid was dissolved in 100 mL of dichloromethane (1.2 equiv. total Meldrum's acid was added) and also filtered. This solution was transferred to a 3.0 L round bottom flask and cooled in an ice water bath. 114 mL (1.42 mole, 2.5 equiv.) of pyridine was added quickly to the magnetically stirred solution. The acid chloride solution was added dropwise at about two drops per second. The solution became characteristically crimson and was stirred overnight, coming to room temperature during that time.

The reaction was then poured into a 4000 mL separatory funnel containing 500 mL of crushed ice and 300 mL of 6N HCl. After vigorous shaking the layers were allowed to separate, and after removing the organic layer the aqueous phase was extracted with three portions of 100 mL dichloromethane. The organic phase was washed with 300 mL of saturated aqueous sodium chloride. The aqueous wash was then extracted with the three 100 mL portions of dichloromethane. The combined organics were dried with 100 g $Na_2SO_4$ and 30 g $MgSO_4$, filtered, and the solvent removed on the rotovap. This resulted in 288.1 g of material (272.5 g theoretical), which was taken up in 2000 mL of methanol. This solution was brought to reflux, with magnetic stirring under an inert atmosphere, and thus reacted for 4 hours. The methanol was then removed on the rotovap to obtain 234.5 g of dark red material.

This dark red material was dissolved in 100 mL of 15% ethyl acetate/hexane, and the minimum amount of ethyl acetate required to dissolve all of the material. This solution was then applied to a 500 g plug of silica gel, and five 500 mL hexane fractions were taken followed by five 500 mL fractions with ethyl acetate. Those fractions containing the product were condensed on the rotovap. Those containing only lower Rf materials were discarded. This product amounted to 232 g of yellow oil which was taken up in 1000 mL of hot 5% ethyl acetate/hexane. On cooling some material precipitated and thus 40 mL (4%) of ethyl acetate was added to redissolve the solids. This solution was loaded onto a HPLC instrument, eluted with 6% ethyl acetate (3 gal. ethyl acetate per 55 gal. drum of hexane), and 5 gal. fractions were taken. The fractions containing the desired product (S)-3-oxo-4-[3,4-dihydro-2,5,7,8-tetramethyl-6(phenylmethoxy)-2H-1-benzopyran-2-yl]butanoic acid methyl ester were condensed with a 5 L Buchi rotovapor, to give 174.9 g (75%) of the desired product after crystallizing from methanol (2000 mL methanol and then water added to cloud point, warmed, water added to cloud point, warmed). The solution was then cooled with mechanical stirring overnight. The 153.6 g of crystals of the desired product thus formed were filtered and dried under vacuum. Additional water was added to the cloud point and warmed twice but did not result in additional crystals. The aqueous methanol solution was condensed and then extracted with three portions of 100 mL dichloromethane. Combining these and then removing the solvent resulted in 5.0 g of impure product. The rotation of recrystallized desired product was $[\alpha]_D^{25} = 15.29°$ C. (c=2.54% in $CHCl_3$) i.e. 97.45% optical purity, determined to be one enantiomer by NMR and shift reagents at 400 MHz. The m.p. was 86°–87° C. EXAMPLE 33

(2S,4′R,8′R)-6-Benzyloxy-2-(3′carbomethoxy-2′oxo-4′,8′,12′-trimethyl-5′,11′-tridecadienyl)-2,5,7,8-tetramethylchroman 18.00 g (0.37 mole) of 50% NaH was weighed into a 3000 mL three-necked flask equipped with magnetic stirrer, septum, and two vacuum take-offs; one takeoff connected to a mineral oil bubbler, and the other connected to the vacuum/argon manifold. The flask was purged three times, evacuating and then flushing with argon. The NaH was washed with three portions of 50 mL of hexane which were added by syringe, stirred, allowed to settle, and then removed by syringe. The flask was then evacuated to near dryness and an argon atmosphere was added. Following this, 100 mL of anhydrous THF (sodium/benzophenone ketyl) was added by syringe.

153.6 g (0.37 mole) of (S)-3-oxo-4-[3,4-dihydro-2,5,7,8-tetramethyl-6-(phenylmethoxy)-2H-1-benzopyran-2-yl]butanoic acid methyl ester was weighed into a 500 mL Schlenk tube, equipped with stir bar and septum. The flask was purged three times, and then 300 mL of anhydrous THF was transferred from the THF still to this flask by cannula. (The cannula was first blown through with argon from the THF still, and then connected to the Schlenk tube). A slight vacuum was applied to the Schlenk tube to facilitate THF transfer. The starting material was fully dissolved within 10 minutes of stirring. During this time a positive pressure or argon was maintained.

The above solution was then transferred to the NaH slurry by cannula. Here again positive argon pressure in the Schlenk tube, and a slight vacuum in the reaction flask facilitated the transfer. The take off valve leading to the bubbler was closed before any vacuum was applied to the reaction flask. The rate of addition was monitored to keep the gas evolution from being too vigorous. Several times the gas was bled off with the vacuum to sustain the flow.

During the addition, the reaction flask did become warm, but no cooling was used. Finally, 50 mL of anhydrous THF was added by syringe to the Schlenk tube (as a wash) and this wash was also flushed through the cannula. Once pressure was equalized, the bubbler was again opened and positive pressure maintained while the subsequent solutions were prepared.

95.9 g (0.37 mole) of methyl (2R,6R,3E)-6,10-dimethyl-3,9-undecadien-2-yl carbonate was weighed into a 250 mL Schlenk tube equipped with stir bar and septum. This system was purged three times, and then 50 mL of anhydrous THF was added by syringe.

5.0 g (0.0043 mole, 1.1%) of Pd(PPh$_3$)$_4$ was quickly transferred from the ampule it was shipped in into a 500 mL Schlenk tube equipped with stir bar and septum. The system was purged three times. Then 200 mL of anhydrous THF was transferred to the flask by syringe, and the catalyst dissolved with stirring to give a lime green solution.

The NaH/ketoester solution in the main reaction vessel was now cooled to about −78° C. with a dry ice/acetone bath. While maintaining positive argon pressure, the cannula was disconnected at the ketoester Schlenk tube and connected to the carbonate Schlenk tube. The main vessel bubbler was closed, and by applying a slight vacuum the carbonate solution was transferred to the main reaction flask. 50 mL of anhydrous THF was added (as a wash) to this Schlenk tube by syringe and this wash was passed through the cannula to the reaction flask.

After pressure equalization and with positive argon pressure the cannula was disconnected at the carbonate Schlenk tube and quickly connected to the catalyst Schlenk tube. In the same manner, a partial vacuum applied to the reaction vessel aided the transfer of the catalyst to the reaction flask. The catalyst Schlenk tube was washed with 50 mL of anhydrous THF, which was added by syringe and then passed through the cannula to the reaction flask.

After stirring under argon overnight, the reaction was diluted with 500 mL of hexane and then quenched with 150 mL of 3N HCl added to 500 mL of crushed ice, all of which was poured into the reaction mixture. Gas was evolved as the acid solution was added. After vigorous mixing in a 4000 mL separatory funnel the layers separated, and the organic layer was washed with 500 mL of saturated aqueous sodium chloride. The aqueous layer was extracted with three 500 mL portions of hexane, then 100 mL of dichloromethane which dissolved the last traces of solids, believed to be organic. The combined organics were dried with 200 g MgSO$_4$, filtered, and condensed on the rotovap. After pumping, the crude mass weighed 243.2 g (220.32 g theoretical). A parallel reaction conducted at the same time on a slightly smaller scale yielded 158.3 g (147.21 g theoretical). These two samples were combined, dissolved in 100 mL of 25% ethyl acetate/hexane, and eluted through a 1000 g plug of silica gel with 25% ethyl acetate/hexane, collecting 1000 mL fractions. The fractions containing product were condensed, made up to 1000 mL and loaded onto a Separations Technologies Lab 1000 Prep LC. The product (2S,4′R,8′R)-6-benzyloxy-2-(3′-carbomethoxy-2′-oxo-4′,8′,12′ trimethyl-5′,11′-tridecadienyl)-2,5,7,8-tetramethylchroman was eluted with 5% ethyl acetate/hexane giving 352.5 g (96%) of crystal clear golden oil.

NOTE: At all times when there is any piercing of septa, or removal of syringe needles or cannula, care was taken to maintain a positive pressure of argon, so as to exclude oxygen from the reaction.

EXAMPLE 34

Preparation of (2S,2′RS,4′R,8′R)-6-Benzyloxy-2-(3′carbomethoxy-2′hydroxy-4′,8′,12′-trimethyl-5′,11′-tridecadienyl)-2,5,7,8-tetramethylchroman 350.0 g (0.59 mole) of the coupled ketoester i.e. (2S,4′R,8′R)-6-benzyloxy-2-(3′-carbomethoxy-2′-oxo 4′,8′,12′-trimethyl-5′,11′-tridecadienyl)-2,5,7,8-tetramethylchroman was dissolved in 4,000 mL of methanol, with 100 mL of ether added as a cosolvent to facilitate dissolution, in a 12 L flask equipped with a mechanical stirrer. 9.25 g (0.59 mole) of NaBH$_4$ was added. After 1 hour the reaction mixture was analyzed by TLC (25% ethyl acetate/hexane) against starting material. Not being complete, another 9.25 g portion of NaBH$_4$ was added. After another hour, by TLC, the reaction was still incomplete. Five subsequent portions of NaBH$_4$ were added. The reaction was then stirred for two days unattended. TLC after that time showed a little starting material still present. The solution was condensed to a volume less than 1,000 mL and a final portion of NaBH$_4$ was added (8 mole equiv. total).

After stirring for 2 hours there was still a trace of starting material but the reaction was essentially complete. The reaction was quenched by slow addition of 500 mL of 3N HCl to the stirring solution. The mixture was extracted with five portions of 1:1 pet. ether:ether. The combined organics were dried with 200 g MgSO$_4$, filtered, and the solvent removed under vacuum. After pumping off residual solvent 350.9 g (99.9%) of the hydroxy ester i.e. (2S,2′RS,4′R,8′R)-6-benzyloxy-2-(3′-carbomethoxy-2′-hydroxy-4′,8′,12′-trimethyl-5′,11′-tridecadienyl)-2,5,7,8-tetramethylchroman as a viscous white oil was obtained.

350.6 g (0.59 mole) of this hydroxy ester was dissolved in 1,000 mL of methanol, adding 50 mL ether to get the material into solution. Then 47.5 g (1.19 mole, 2 equiv.) of sodium hydroxide was dissolved in 1,000 mL of methanol, and 18 mL of water. These were mixed in a 5 mL flask equipped with a mechanical stirrer. After stirring at reflux for 3 hours, little reaction had occurred and a second 47.5 g portion of sodium hydroxide was added in 36 mL of water. 500 mL THF (distilled) and 500 mL water were also added and the solution was brought to reflux for 3 hours. The solution was milky white. Refluxing clarified the solution, and as it did, at 1 hour intervals three 100 mL portions of water were added to the solution causing cloudiness to reappear.

At the end of this time the reaction was still not complete by TLC (25% ethyl acetate/hexane, then a third 47.5 g portion of sodium hydroxide was added and the reaction was refluxed overnight (6 equiv. NaOH total, 850 mL H$_2$O total, 500 mL THF, 2,000 mL MeOH). The cooled solution was condensed as much as possible on the rotovap using house vacuum. Then 500 mL of 6N HCl (cold) was slowly added to the cold stirring solution. The hydroxy acid was extracted with three 500 mL portions of dichloromethane. The combined organics were dried with 200 g MgSO$_4$, Filtered, and condensed on the rotovap. After pumping off residual solvents, 350.6 g (>100% yield) of the title product was obtained which later solidified.

EXAMPLE 35

Preparation of the Benzyl Ether of (2S,4'R,8'R)-2',5',11'-α-Tocotrienol

The hydroxy acid product of Example 34, (2S,2'RS,4'R,8'R)-6-benzyloxy-2-(3'-carboxy-2'-hydroxy-4',8',12'-trimethyl-5',11'-tridecadienyl)-2,5,7,8-tetramethylchroman, 350.6 g, was dissolved in 1,000 mL of toluene in a 3.0 L three-neck flask equipped with a thermometer, magnetic stirrer, and topped with a Dean-Stark trap and condenser. The solution was brought to reflux, and the first 20 mL of distillate was removed. Cloudy as it was, no water separated. Then the solution was cooled to 60° C. and the Dean-Stark trap was replaced with a 1,000 mL pressure equalizing addition funnel. 120.65 g of di-tert. butyl-dimethylformamide acetal was added to the addition funnel. This reagent was added dropwise to the stirring solution, which vigorously evolved gas and foamed. After complete addition the reaction was stirred overnight, allowing the reaction to cool. TLC (25% ethyl acetate/hexane) showed that the reaction was not complete.

The reaction was warmed again to 60° C. and checked after 2 hours. At this point a second 120.65 g (0.59 mole, 1.0 equiv.) of the di-t-butyl-dimethylformamide acetal was added, by slow dropwise addition. Again there was vigorous gas evolution and foaming. After 3 hours stirring at 60° C. the reaction was determined to be complete by TLC. There were two major high Rf products and at least four minor low Rf products. The solvent was removed on the rotovap at 60° C. with house vacuum. This resulted in 340 g of crude yellow oil. This was taken up in 100 mL of 5% ethyl acetate/hexane and passed through a 1,000 g plug of silica gel with 10% ethyl acetate/hexane. 500 mL fractions were taken, and all except those containing only very polar material were combined and concentrated. This material was diluted to 1,000 mL with 5% ethyl acetate/hexane and loaded onto the preparative liquid chromatography column. The desired product, the benzyl ether of (2R,4'R,8'R)-2',5',11'-α-tocotrienol, eluted with ethyl acetate/95% hexane. The refractive index detector was marginally useful in deciding where to cut the fractions. Basically, 20 L fractions were taken. After condensing the appropriate fractions on the 5 L rotovap, 140.2 g (45.9% yield) of pure product SYN: [2S,4'R,2(E/Z),5(E),8'R]-3,4-dihydro-2,5,7,8-tetramethyl-2-(4,8,12-trimethyl-2,5,11-tridecatrienyl)-6-(phenylmethoxy-2H-1-benzopyran (highest Rf material), was obtained.

EXAMPLE 36

Preparation of Vitamin E 126.0 g (0.24 mole) of the [2S,4'R,2(E/Z),5(E),8'R]-3,4-dihydro-2,5,7,8-tetramethyl-2(4',8',12'-trimethyl-2',5',11'-tridecatrienyl)-6-(phenylmethoxy)-2H-1-benzopyran viz. benzyl ether of (2S,4'R,8'R)-2',5',11'-α-tocotrienol was dissolved in 1000 mL of ethyl acetate. This was hydrogenated at 500 psi with 6.3 g of platinum on carbon at 25° C. After 4 hours the uptake of hydrogen was complete. Filtration and solvent removal under vacuum resulted in 126.5 g (99.2%) of Vitamin E benzyl ether.

126.0 g of the Vitamin E product prepared above was dissolved in 600 mL of 100% ethanol, and 50 mL of dry THF was added to get all of the material into solution. 10 g of (10%) palladium on carbon was added as catalyst and the solution was hydrogenated at 60 psi for 4 hours at which time hydrogen uptake was complete.

TLC of the reaction showed cleanly one spot, and the solvent phase was colorless. On filtering in air and condensing the material at 40° C. on the rotovap using aspirator vacuum, the product picked up cloudiness and became brown in color. This product weighed 110.1 g (~100% crude yield). This material was dissolved in 100 mL of 5% ethyl acetate/hexane which was saturated with argon. This solution was applied to a 500 g plug of silica gel and flash eluted with 5% ethyl acetate/hexane (argon saturated) using argon as the pressurizing gas. The 500 mL fractions taken were covered, and quickly sealed after removal from the collection point. At the time of the chromatography several impurities (minor) were seen in some of the fractions. The major product amount 89.3 g (86% yield) of pure (one spot) material was obtained by condensing the appropriate fractions and then pumping at $10^{-5}$ mm for 4 days. The other fractions were condensed, and pumped down and amounted to 8.6551 g (8.3%) (i.e. 94% total yield).

EXAMPLE 37

Preparation of (S)-1-[3,4-Dihydro-2,5,7,8-tetramethyl-6-(phenylmethoxy)-2H-1-benzopyran-2-yl]-3-(phenylsulfonyl)-2-propanone Methyl (S)-[3,4-dihydro-2,5,7,8-tetramethyl-6-(phenylmethoxy)-2H-1-benzopyran-2-yl]-acetate (25.8 g, 0.070 mole) was dissolved in 50 mL of dry THF contained in a 500 mL three-neck flask equipped with a magnetic stirring bar and argon inlet and outlet adaptors. The flask was swept with argon.

Methyl phenylsulfone (10.94 g, 0.070 mole) was weighed into a 300 mL Schlenk tube equipped with a stirring bar and septum. The Schlenk tube was evacuated, refilled with argon, and charged with 150 mL of dry THF, using a syringe. The Schlenk tube and contents were chilled to 0°. A solution of 2.6M butyl lithium in hexane (2×27 mL=0.1404 mole) was added from a syringe in two portions. The second addition produced a creamy orange slurry of the dianion. After stirring for 15 minutes, this mixture was transferred via cannula to the three-neck flask containing the ester in THF. A 50 mL portion of THF was used to complete the transfer. After stirring the resulting mixture for 2 hours, the reaction mixture had warmed to room temperature and was quenched with 40 mL of 2N HCl. This mixture was transferred to a 1L separatory funnel. Hexane (100 mL) and brine (50 mL) were added and, after shaking, the layers were separated. The aqueous layer was extracted with 3×30 mL of $CH_2Cl_2$. The combined organic layers were dried over $MgSO_4$ and evaporated to a solid residue of crude product (43.7 g). This material was recrystallized from 500 mL of ethanol giving 31.3 g (90.8% yield) of (S)-1-[3,4-dihydro-2,5,7,8-tetramethyl-6-(phenylmethoxy)-2H-1-benzopyran-2-yl]-3-(phenylsulfonyl)-2-propanone as a pale yellow solid. A second crop of 4.0 g of less pure material was also obtained, but kept separate.

An analytical sample was recrystallized from ethanol to give colorless crystals with m.p. 130°–8° and $[\alpha]_D = +14.09°$ (c=0.9225, $CHCl_3$).

EXAMPLE 38

Preparation of
(2S,4′R,5′E,8′R)-1-[3,4-Dihydro-2,5,7,8-tetramethyl-6-(phenylmethoxy)-2H-benzopyran-2-yl]-4′,8′,12′-trimethyl-3′-(phenylsulfonyl)-trideca-5′,11′-dien-2′-one A 300 mL Shlenk tube containing a stirring bar was charged with 16.0 g (0.0325 mole) of (S)-1-[3,4-dihydro-2,5,7,8-tetramethyl-6-(phenylmethoxy)-2H-1-benzopyran-2-yl]-3-(phenylsulfonyl)-2-propanone and closed with a septum. The tube was evacuated and refilled with argon. A 50 mL portion of dry THF was then added from a syringe; giving a clear solution.

A 1 L three-neck flask was set up with a stirring bar, argon inlet and exit adapters, and a septum to seal the center neck. This flask was charged with 1.559 g (0.0325 mole) of NaH, 50% in oil. Two 10 mL portions of hexane were used to wash out the oil, a syringe being used to remove the hexane after the solid NaH had settled. The flask was filled with argon and charged with 100 mL of dry THF. The solution in the Schlenk tube was then transferred in via cannula, using 50 mL of dry THF to complete the transfer. A solution of 8.327 g (0.0325 mole) of allylic carbonate which was methyl (2R,6R,3E)-6,10-dimetyl-3,9-undecadien-2-yl carbonate in 10 mL of dry THF was prepared in a 100 mL Schlenk tube under argon. The main reaction flask was then chilled in a dry ice/acetone bath and the allylic carbonate solution was then transferred in via cannula, some rinse THF being used to complete the transfer. A solution of the catalyst, 1.126 g (0.000974 mole, 3 mole percent) of palladium tetrakis(triphenylphosphine) in 100 mL of dry THF was prepared under argon in a 100 mL Schlenk tube. This solution was also transferred to the main reaction flask via cannula.

The reaction mixture was allowed to stir overnight, during which time it warmed to room temperature. By TLC analysis of a 0.2 mL aliquot (partitioned between ether and 1N HCl), the reaction was judged to be complete.

The reaction was then quenched by adding 40 mL of 2N HCl and 100 mL of brine, followed by 100 mL of hexane.

The mixture was transferred to a separatory funnel and shaken. The organic layer was separated and the aqueous layer was extracted with 3×25 mL of $CH_2Cl_2$. The combined organic layers were dried over $MgSO_4$, filtered, and stripped of solvent under reduced pressure. The 26.8 g of crude product which was (2S,4′R,5′E,8′R)-1′-[3,4-dihydro-2,5,7,8-tetramethyl-6-(phenylmethoxy)-2H-benzopyran-2-yl]-4′,8′,12′-trimethyl-3′-(phenylsulfonyl)-trideca-5′,11′-dien-2′-one was taken up in 5% EtOAc/hexane and applied to a 100 g plug of Florisil. The product was eluted with 5% EtOAc/hexane and collected in 50 mL fractions. The first six contained a less polar product and were discarded. Fractions 7–10 afforded 17.6 g of product containing a slight impurity at higher Rf. Fractions 11–30 afforded 3.7 g of analytically pure product. Both were viscous, colorless oils, total yield of (2S,4′R,5′E,8′R)-1′-[3,4-dihydro-2,5,7,8-tetramethyl-6-(phenylmethoxy)-2H-benzopyran-2-yl]-4′,8′,12′-trimethyl-3′-(phenylsulfonyl)-trideca-5′,11′-dien-2′-one, 21.3 g (97.7%).

EXAMPLE 39

Preparation of
(2S,4′R,5′E,8′R)-1′-[3,4-Dihydro-2,5,7,8-tetramethyl-6-(phenylmethoxy)-2H-1-benzopyran-2-yl]-2′-hydroxy-4′,8′,12′-trimethyl-3′-(phenylsulfonyl)trideca-5′,11′-diene A solution of (2S,4′R,5′E,8′R)-1′-[3,4-dihydro-2,5,7,8-tetramethyl-6-(phenylmethoxy)-2H-benzopyran-2-yl]-4′,8′,12′-trimethyl-3′-(phenylsulfonyl)-trideca-5′,11′-dien-2′-one (3.7 g) in 80 mL of toluene was cooled to 0° and treated, while stirring, dropwise during 2 minutes, with 6.7 mL of a 25% solution of diisobutylaluminum hydride (DIBAL) in toluene.

After 1 hour of stirring at 0°, the reaction was quenched by adding 20 mL of 3N HCl. Stirring was continued for 30 minutes. After transfer to a separatory funnel, the organic layer was separated, washed with water, dried over $Na_2SO_4$ and evaporated. The product (2S,4′R,5′E,8′R)-1′-[3,4-dihydro-2,5,7,8-tetramethyl-6-(phenylmethoxy)-2H-1-benzopyran-2-yl]-2′-hydroxy-4′,8′,12′-trimethyl-3′-(phenylsulfonyl)trideca-5′,11′-diene was obtained as a colorless oil, 3.85 g.

EXAMPLE 40

Preparation of
(2S,4′R,5′E,8′R)-1′-[3,4-Dihydro-2,5,7,8-tetramethyl-6-(phenylmethoxy)-2H-1-benzopyran-2-yl]-2′-methanesulfonyloxy-4′,8′,12′-trimethyl-3′-(phenylsulfonyl)trideca-5′,11′-diene The compound (2S,4′R,5′E,8′R)-1′-[3,4-dihydro-2,5,7,8-tetramethyl-6-(phenylmethoxy)-2H-1-benzopyran-2-yl]-2′-hydroxy-4′,8′,12′-trimethyl-3′-(phenylsulfonyl)trideca-5′,11′-diene (3.6 g) was taken up in 50 mL of pyridine, treated with 3 mL of methanesulfonyl chloride, and stirred at room temperature for 20 hours. The pyridine was evaporated off under reduced pressure. The residue was stirred with 200 mL of hexane and the hexane then evaporated. An additional 200 mL of hexane was added and the insoluble material was filtered off and washed with ether. The filtrate and washing were combined and evaporated, finally under high vacuum, to leave 3.9 g of (2S,4′R,5′E,8′R)-1′-[3,4-dihydro-2,5,7,8-tetramethyl-6-(phenylmethoxy)-2H-1-benzopyran-2-yl]-2′-methanesulfonyloxy-4′,8′,12′-trimethyl-3′-(phenylsulfonyl)trideca-5′,11′-diene as a yellow gum.

EXAMPLE 41

Preparation of
(2S,4′R,5′E,8′R)]-1′-[3,4-Dihydro-2,5,7,8-tetramethyl-6-(phenylmethoxy)-2H-1-benzopyran-2-yl]-4′,8′,12′-trimethyl-3′-(phenylsulfonyl)trideca-2′,5′,11′-triene The compound of (2S,4′R,5′E,8′R)-1′-[3,4-dihydro-2,5,7,8-tetramethyl-6-(phenylmethoxy)-2H-1-benzopyran-2-yl]-2′-methanesulfonyloxy-4′,8′,12′-trimethyl-3′-(phenylsulfonyl)trideca-5′,11′-diene (3.9 g) was taken up in 75 mL of ether and treated with 2.5 mL of 1,5-diazabicyclo[4.3.0]-non-5-ene (DBN) and stirred at room temperature for 20 hours. An additional 0.5 mL of DBN was added and stirring was continued overnight. A tlc analysis at this point showed the elimination to be complete. The reaction mixture was washed successively with 1N HCl and aqueous $NaHCO_3$, then dried over $Na_2SO_4$ and evaporated. The (2S,4′R,5′E,8′R)-1′-[3,4-dihydro-2,5,7,8-tetramethyl-6-

(phenylmethoxy)-2H-1-benzopyran-2'-yl]-4',8',12'-trimethyl-3'-(phenylsulfonyl)trideca-2',5',11'-triene was obtained as a residue, 3.4 g of pale yellow oil.

EXAMPLE 42

Preparation of the Benzyl Ether of (2S,4'R,8'R)-2',5',11'-α-Tocotrienol

The compound of (2S,4'R,5'E,8'R)-1'-[3,4-dihydro-2,5,7,8-tetramethyl-6-(phenylmethoxy)-2H-benzopyran-2-yl]-4',8',12'-trimethyl-3'-(phenylsulfonyl)trideca-2',5',11'-triene (3.4 g) was taken up in 100 mL of cyclohexane. To this solution 100 mL of water, 1.0 g of "Aliquot 336" phase transfer reagent, 3.5 g of NaHCO$_3$, and 3.0 g of sodium dithionite (Na$_2$S$_2$O$_4$) were added. The mixture was stirred and heated to reflux for 1½ hours. Then an additional 1.0 g of Na$_3$S$_2$O$_4$ was added followed by a further 1 hour of reflux. A final addition of 0.5 g of Na$_2$S$_2$O$_4$ was followed by 30 minutes of reflux and stirring at room temperature overnight. The mixture was transferred to a separatory funnel and the organic layer was removed. The aqueous layer was extracted with hexane and the combined organic layers were washed with water, dried over Na$_2$S$_2$O$_4$ and stripped of solvent under reduced pressure. The residue was chromatographed on silica gel using 5% EtOAc/hexane as the eluent. The fractions containing the product were combined and evaporated leaving 730 mg (27.3%) of (2S,2'E,4'R,5'E,8'R)-1'-[3,4-dihydro-2,5,7,8-tetramethyl-6-(phenylmethoxy)-2H-1-benzopyran-2-yl]-4',8',12'-trimethyltrideca-2',5',11'-triene as a colorless oil. SYN: benzyl ether of (2S,4'R,8'R)-2',5',11'-α-Tocotrienol).

EXAMPLE 43

Preparation of d-α-Tocopherol

The triene (2S,2'E,4'R,5'E,8'R)-1'-[3,4-dihydro-2,5,7,8-tetramethyl-6-(phenylmethoxy)-2H-1-benzopyran-2-yl]-4',8',12'-trimethyltrideca-2',5',11'-triene (730 mg) was dissolved in 15 mL of ethyl acetate, mixed with 60 mg of 10% Pt/C and hydrogenated at 8° C. overnight under 500 psi of hydrogen. The catalyst was filtered and washed and the filtrate evaporated to leave 630 mg of d-α-tocopheryl benzyl ether. The benzyl ether of d-α-tocopherol (630 mg) was debenzylated by hydrogenation in ethanol/THF (10 mL of a 9:1 parts by volume mixture) over 10% Pd/C (80 mg) at 8° C. for 3 hours under 60 psi of hydrogen.

The catalyst was filtered and washed and the clear, colorless filtrate was evaporated; all under argon with minimal exposure to air. The residue of 510 mg d-α-tocopherol acquired a pale brownish color on storage.

What is claimed is:

1. A compound of the formula:

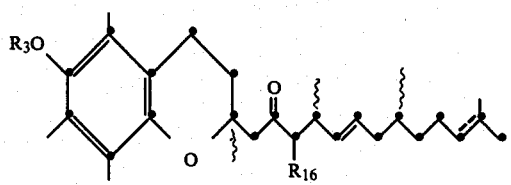

wherein R$_{16}$ is hydrogen, —COOR$_4$ or

the dotted line forms either a saturated single or an unsaturated double bond; R$_3$ taken together with its attached oxygen forms an ether hydroxy protecting group; R$_4$ is lower alkyl and R$_6$ is lower alkyl or aryl.

2. The compound of claim 1 wherein R$_3$ is benzyl.

3. The compound of claim 1 wherein R$_{16}$ is hydrogen.

4. The compound of claim 2 wherein R$_{16}$ is —COOR$_4$.

5. The compound of claim 2 wherein R$_{16}$ is

6. A compound of the formula:

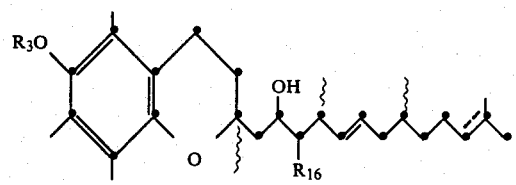

wherein R$_{16}$ is

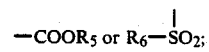

R$_5$ is hydrogen or lower alkyl; R$_6$ is lower alkyl or aryl; R$_3$ taken together with its attached oxygen atom forms an ether hydroxy protecting group; and the dotted line forms either a saturated single bond or an unsaturated double bond.

7. The compound of claim 6 wherein R$_{16}$ is —COOR$_5$.

8. The compound of claim 7 wherein R$_3$ is an aralkyl.

9. The compound of claim 6 wherein R$_{16}$ is

10. The compound of claim 9 wherein R$_3$ is aralkyl.

11. The compound of claim 3 wherein said compound is 1-[3,4-dihydro-2,5,7,8-tetramethyl-6-[phenylmethoxy]-2H-1-benzopyran-2-yl]-4',8',12'-trimethyl-5'-tridecen-2',one.

12. The compound of claim 4 wherein said compound is 6-benzyloxy-2-(3'-carbomethoxy-2'-oxo-4',8',12'-trimethyl-5'-tridecenyl)-2,5,7,8-tetramethylchroman.

13. The compound of claim 4 wherein said compound is 6-benzyloxy-2-(3'-carbomethoxy-2'-oxo-4',8',12'-trimethyl-5',11'-tridecadienyl)-2,5,7,8-tetramethylchroman.

14. The compound of claim 5 wherein said compound is 1'-[3,4-dihydro-2,5,7,8-tetramethyl-6-(phenylmethoxy)-2H-1-benzopyran-2-yl]-4',8',12'-trimethyl-3'-(phenylsulfonyl)trideca-5,11'-diene-2'-one.

15. The compound of claim 7 wherein said compound is 6-benzyloxy-2-(3'-carbomethoxy-2'-hydroxy-4',8',12'-trimethyl-5',11'-tridecadienyl)-2,5,7,8-tetramethylchroman.

16. The compound of claim 9 wherein said compound is 1'-[3,4-dihydro-2,5,7,8-tetramethyl-6-(phenylmethoxy)-2H-1-benzopyran-2-yl]2'-hydroxy-b 4',8',12'-trimethyl-3'-(phenylsulfonyl)-trideca-5',11'-diene.

* * * * *